US008753698B2

(12) United States Patent
Van Amerongen et al.

(10) Patent No.: US 8,753,698 B2
(45) Date of Patent: Jun. 17, 2014

(54) ANTI-HYPERTENSIVE FUNCTIONAL FOOD PRODUCTS

(75) Inventors: Aart Van Amerongen, Veenendaal (NL); Maria Josepha Catharina Beelen-Thomissen, Oss (NL); Arie Van der Bent, Tiel (NL); Jan Hendrik Buikema, Groningen (NL); Wiekert Hendrikus Van Gilst, Haren (NL); Maria Henrieette Johanna Loonen, Oirlo (NL); Karin Beatrice Merck, Oss (NL); Jos Nelissen, Oirlo (NL); Wilhelmus Johannes Gertrudes Thielen, Venray (NL); Klaas Arnoud Togtema, Uden (NL)

(73) Assignee: Globus Egg Sciences B.V., Oirlo (NL)

( * ) Notice: Subject to any disclaimer, the term of this patent is extended or adjusted under 35 U.S.C. 154(b) by 1282 days.

(21) Appl. No.: 11/632,889

(22) PCT Filed: Jul. 22, 2005

(86) PCT No.: PCT/NL2005/000535
§ 371 (c)(1),
(2), (4) Date: Aug. 22, 2008

(87) PCT Pub. No.: WO2006/009448
PCT Pub. Date: Jan. 26, 2006

(65) Prior Publication Data
US 2009/0029005 A1 Jan. 29, 2009

Related U.S. Application Data

(60) Provisional application No. 60/589,902, filed on Jul. 22, 2004.

(30) Foreign Application Priority Data

Jan. 27, 2005 (EP) .................................. 05100544

(51) Int. Cl.
A23L 1/28 (2006.01)
A23L 1/305 (2006.01)
A23J 3/34 (2006.01)
A61K 38/38 (2006.01)
A61K 38/47 (2006.01)
A61K 35/54 (2006.01)
A61K 38/40 (2006.01)
A61K 38/01 (2006.01)

(52) U.S. Cl.
CPC .............. *A61K 35/54* (2013.01); *A23L 1/3053* (2013.01); *A23J 3/341* (2013.01); *A61K 38/38* (2013.01); *A61K 38/47* (2013.01); *A23V 2002/00* (2013.01); *A61K 38/40* (2013.01); *A61K 38/012* (2013.01)
USPC ........................................... 426/63; 426/614

(58) Field of Classification Search
None
See application file for complete search history.

(56) References Cited

U.S. PATENT DOCUMENTS

| 5,711,985 | A | 1/1998 | Guerrero et al. | |
|---|---|---|---|---|
| 6,514,941 | B1 | 2/2003 | Tolton, II et al. | |
| 2002/0106704 | A1 * | 8/2002 | Lal et al. | ...................... 435/7.21 |

FOREIGN PATENT DOCUMENTS

| EP | 0357776 A1 | 5/1988 | |
|---|---|---|---|
| EP | 0274946 A1 | 7/1988 | |
| EP | 0 357 776 | * 3/1990 | ............. C07K 15/00 |
| EP | 0 357 776 A1 * | 3/1990 | ............. C07K 15/00 |
| EP | 0583074 A2 | 2/1994 | |
| EP | 0677249 A2 | 2/1995 | |
| EP | 1094071 A1 | 4/2001 | |
| EP | 1228708 A2 | 8/2002 | |
| JP | 3280835 A | 12/1991 | |
| JP | 04152892 | 5/1992 | |
| JP | 04202200 | 7/1992 | |
| JP | 04247098 | 9/1992 | |
| JP | 04247100 | 9/1992 | |
| JP | 05331190 | 12/1993 | |
| JP | 10036394 | 2/1998 | |
| JP | 2001061445 A | 3/2001 | |
| KR | 2003 0003463 | * 1/2003 | |
| KR | 2003003463 A | * 1/2003 | ............. A61K 38/00 |
| KR | 20030003463 | 10/2003 | |
| WO | 0132905 A1 | 5/2001 | |
| WO | 0185984 A1 | 11/2001 | |

OTHER PUBLICATIONS

Matoba et al "A novel anti-hypertensive peptide derived from ovalbumin induces nitric oxide-mediated vasorelaxation in an isolated SHR mesenteric artery," FEBS Letters 452 (1999).*
Kato et al "Deamidation of Food Proteins by Protease in Alkaline pH," J. Agric. Food Chem. 1987, 35, 224-227).*
Canfield "Peptides derived from Tryptic Digestion of Egg White Lysozyme," JBC 288(8): 2691-2697 1963.*
Kato et al., "Deamidation of Food Proteins by Protease in Alkaline pH", J. Agric. Food Chem, 1987, pp. 224-227, vol. 35.
Fujita et al., "Classification and Antihypertensive Activity of Angiotensin I-Converting Enzyme Inhibitory Peptides Derived from Food Proteins", Journal of Food Science, 2000, pp. 564-569, vol. 65, No. 4.
Matoba et al., "A novel anti-hypertensive peptide derived from ovalbumin induces nitric oxide-mediated vasorelaxation in an isolated SHR mesenteric artery", Federation of European Biochemical Societies, Jul. 6, 1999, pp. 181-184, FEBS vol. 452.

(Continued)

*Primary Examiner* — Suzanne Ziska
(74) *Attorney, Agent, or Firm* — The Webb Law Firm

(57) ABSTRACT

The present invention provides novel protein hydrolysates with anti-hypertensive properties, as well as food products and food supplements comprising these.

13 Claims, No Drawings

(56) References Cited

OTHER PUBLICATIONS

Fujita et al., "Isolation and Characterization of Ovokinin, a Bradykinin B1 Agonist Peptide Derived from Ovalbumin", Peptides, 1995, pp. 785-790, vol. 16, No. 5.

Hiidenhovi et al., "Hen Egg White Ovomucin, a Potential Ingredient for Functional Foods", Special Publication Royal Society of Chemistry, 2000, No. 248, pp. 197-199.

Research Document on Agriculture, Forestry and Fisheries, Object No. 30, "Research on Biological Regulation Function of Food" (issued on Mar. 16, 2004) edited and published by Technical Convention Office of Ministry of Agriculture, Forestry and Fisheries of Japan. pp. 127-134.

Henikoff et al., "Amino Acid Substitution Matrices from Protein Blocks", Proc. Natl. Acad. Sci. USA, Nov. 1992, vol. 89, pp. 10915-10919.

Siemensma et al., "The Importance of Peptide Lengths in Hypoallergenic Infant Formulae", Trends in Food Science and Technology, Jan. 1993, vol. 4, pp. 16-21.

Kaufmann, "Matrix-assisted Laser Desorption Ionization (MALDI) Mass Spectrometry: a Novel Analytical Tool in Molecular Biology and Biotechnology", Journal of Biotechnology, 1995, vol. 41, pp. 155-175.

MacMahon et al., "Blood Pressure, Stroke, and Coronary Heart Disease", Lancet, 1990, vol. 335, pp. 765-774.

Murray et al., "Alternative Projections of Mortality and Disability by Cause 1990-2020: Global Burden of Disease Study", Lancet, 1997, vol. 349, pp. 1498-1504.

Soeryapranata et al., "Matrix-Assisted Laser Desorption/Ionization Time-of-Flight Mass Spectrometry Method for the Quantification of β-Casein Fragment", J. Food Sci., 2002, vol. 67, pp. 534-538.

Moller et al., "Metabolic Syndrome: a Clinical and Molecular Perspective", Annual Rev. of Medicine, 2005, vol. 56, pp. 45-62.

Terheggen-Lagro et al., "Safety of a New extensively Hydrolysed Formula in Children with Cow's Milk Protein Allergy: a Double Blind Crossover Study", BMC Pediatrics, 2002, vol. 2(10), pp. 1-7.

Van Vliet et al., "Direct and Indirect Methods Used to Study Arterial Blood Pressure", Journal of Pharmacological and Toxicological Methods, 2000, vol. 44, pp. 361-373.

Sekiya et al., "Antihypertensive Effects of Tryptic Hydrolysate of Casein on Normtensive and Hypertensive Volunteers", Journal of Japanese Food Society, 1992, vol. 45(6), pp. 513-517.

Matsui et al., "Colorimetric Measurement of Angiotensin I-Converting Enzyme Inhibitory Activity with Trinitrobenzene Sulfonate", Biosci., Biotech, Biochem., 1992, vol. 56(3), pp. 517-518.

* cited by examiner

```
                        SEQUENCE LISTING

<160> NUMBER OF SEQ ID NOS: 10

<210> SEQ ID NO 1
<211> LENGTH: 234
<212> TYPE: PRT
<213> ORGANISM: unknown
<220> FEATURE:
<223> OTHER INFORMATION: VIT2_CHICK

<400> SEQUENCE: 1

Phe Arg Ser Ala His Arg Gln Glu Phe Pro Lys Arg Lys Leu Pro Gly
1               5                   10                  15

Asp Arg Ala Thr Ser Arg Tyr Ser Ser Thr Arg Ser Ser His Asp Thr
            20                  25                  30

Ser Arg Ala Ala Ser Trp Pro Lys Phe Leu Gly Asp Ile Lys Thr Pro
        35                  40                  45

Val Leu Ala Ala Phe Leu His Gly Ile Ser Asn Asn Lys Lys Thr Gly
    50                  55                  60

Gly Leu Gln Leu Val Val Tyr Ala Asp Thr Asp Ser Val Arg Pro Arg
65                  70                  75                  80

Val Gln Val Phe Val Thr Asn Leu Thr Asp Ser Ser Lys Trp Lys Leu
                85                  90                  95

Cys Ala Asp Ala Ser Val Arg Asn Ala His Lys Ala Val Ala Tyr Val
            100                 105                 110

Lys Trp Gly Trp Asp Cys Arg Asp Tyr Lys Val Ser Thr Glu Leu Val
        115                 120                 125

Thr Gly Arg Phe Ala Gly His Pro Ala Ala Gln Val Lys Leu Glu Trp
    130                 135                 140

Pro Lys Val Pro Ser Asn Val Arg Ser Val Val Glu Trp Phe Tyr Glu
145                 150                 155                 160

Phe Val Pro Gly Ala Ala Phe Met Leu Gly Phe Ser Glu Arg Met Asp
                165                 170                 175

Lys Asn Pro Ser Arg Gln Ala Arg Met Val Val Ala Leu Thr Ser Pro
            180                 185                 190

Arg Thr Cys Asp Val Val Val Lys Leu Pro Asp Ile Ile Leu Tyr Gln
        195                 200                 205

Lys Ala Val Arg Leu Pro Leu Ser Leu Pro Val Gly Pro Arg Ile Pro
    210                 215                 220

Ala Ser Glu Leu Gln Pro Pro Ile Trp Asn
225                 230

<210> SEQ ID NO 2
<211> LENGTH: 1095
<212> TYPE: PRT
<213> ORGANISM: unknown
<220> FEATURE:
<223> OTHER INFORMATION: VIT2_CHICK

<400> SEQUENCE: 2

Lys Phe Asp Ile Asp Pro Gly Phe Asn Ser Arg Arg Ser Tyr Leu Tyr
1               5                   10                  15

Asn Tyr Glu Gly Ser Met Leu Asn Gly Leu Gln Asp Arg Ser Leu Gly
            20                  25                  30
```

-continued

Lys Ala Gly Val Arg Leu Ser Ser Lys Leu Glu Ile Ser Gly Leu Pro
            35                  40                  45

Glu Asn Ala Tyr Leu Leu Lys Val Arg Ser Pro Gln Val Glu Glu Tyr
 50                  55                  60

Asn Gly Val Trp Pro Arg Asp Pro Phe Thr Arg Ser Ser Lys Ile Thr
 65                  70                  75                  80

Gln Val Ile Ser Ser Cys Phe Thr Arg Leu Phe Lys Phe Glu Tyr Ser
                 85                  90                  95

Ser Gly Arg Ile Gly Asn Ile Tyr Ala Pro Glu Asp Cys Pro Asp Leu
             100                 105                 110

Cys Val Asn Ile Val Arg Gly Ile Leu Asn Met Phe Gln Met Thr Ile
             115                 120                 125

Lys Lys Ser Gln Asn Val Tyr Glu Leu Gln Glu Ala Gly Ile Gly Gly
 130                 135                 140

Ile Cys His Ala Arg Tyr Val Ile Gln Glu Asp Arg Lys Asn Ser Arg
145                 150                 155                 160

Ile Tyr Val Thr Arg Thr Val Asp Leu Asn Asn Cys Gln Glu Lys Val
                165                 170                 175

Gln Lys Ser Ile Gly Met Ala Tyr Ile Tyr Pro Cys Pro Val Asp Val
             180                 185                 190

Met Lys Glu Arg Leu Thr Lys Gly Thr Thr Ala Phe Ser Tyr Lys Leu
         195                 200                 205

Lys Gln Ser Asp Ser Gly Thr Leu Ile Thr Asp Val Ser Ser Arg Gln
 210                 215                 220

Val Tyr Gln Ile Ser Pro Phe Asn Glu Pro Thr Gly Val Ala Val Met
225                 230                 235                 240

Glu Ala Arg Gln Gln Leu Thr Leu Val Glu Val Arg Ser Glu Arg Gly
                245                 250                 255

Ser Ala Pro Asp Val Pro Met Gln Asn Tyr Gly Ser Leu Arg Tyr Arg
             260                 265                 270

Phe Pro Ala Val Leu Pro Gln Met Pro Leu Gln Leu Ile Lys Thr Lys
         275                 280                 285

Asn Pro Glu Gln Arg Ile Val Glu Thr Leu Gln His Ile Val Leu Asn
 290                 295                 300

Asn Gln Gln Asp Phe His Asp Asp Val Ser Tyr Arg Phe Leu Glu Val
305                 310                 315                 320

Val Gln Leu Cys Arg Ile Ala Asn Ala Asp Asn Leu Glu Ser Ile Trp
                325                 330                 335

Arg Gln Val Ser Asp Lys Pro Arg Tyr Arg Arg Trp Leu Leu Ser Ala
             340                 345                 350

Val Ser Ala Ser Gly Thr Thr Glu Thr Leu Lys Phe Leu Lys Asn Arg
         355                 360                 365

Ile Arg Asn Asp Asp Leu Asn Tyr Ile Gln Thr Leu Leu Thr Val Ser
 370                 375                 380

Leu Thr Leu His Leu Leu Gln Ala Asp Glu His Thr Leu Pro Ile Ala
385                 390                 395                 400

Ala Asp Leu Met Thr Ser Ser Arg Ile Gln Lys Asn Pro Val Leu Gln
                405                 410                 415

Gln Val Ala Cys Leu Gly Tyr Ser Ser Val Val Asn Arg Tyr Cys Ser
             420                 425                 430

Gln Thr Ser Ala Cys Pro Lys Glu Ala Leu Gln Pro Ile His Asp Leu
         435                 440                 445

-continued

Ala Asp Glu Ala Ile Ser Arg Gly Arg Glu Asp Lys Met Lys Leu Ala
450                 455                 460

Leu Lys Cys Ile Gly Asn Met Gly Glu Pro Ala Ser Leu Lys Arg Ile
465                 470                 475                 480

Leu Lys Phe Leu Pro Ile Ser Ser Ser Ala Ala Asp Ile Pro Val
            485                 490                 495

His Ile Gln Ile Asp Ala Ile Thr Ala Leu Lys Lys Ile Ala Trp Lys
        500                 505                 510

Asp Pro Lys Thr Val Gln Gly Tyr Leu Ile Gln Ile Leu Ala Asp Gln
            515                 520                 525

Ser Leu Pro Pro Glu Val Arg Met Met Ala Cys Ala Val Ile Phe Glu
530                 535                 540

Thr Arg Pro Ala Leu Ala Leu Ile Thr Thr Ile Ala Asn Val Ala Met
545                 550                 555                 560

Lys Glu Ser Asn Met Gln Val Ala Ser Phe Val Tyr Ser His Met Lys
                565                 570                 575

Ser Leu Ser Lys Ser Arg Leu Pro Phe Met Tyr Asn Ile Ser Ser Ala
            580                 585                 590

Cys Asn Ile Ala Leu Lys Leu Leu Ser Pro Lys Leu Asp Ser Met Ser
        595                 600                 605

Tyr Arg Tyr Ser Lys Val Ile Arg Ala Asp Thr Tyr Phe Asp Asn Tyr
610                 615                 620

Arg Val Gly Ala Thr Gly Glu Ile Phe Val Val Asn Ser Pro Arg Thr
625                 630                 635                 640

Met Phe Pro Ser Ala Ile Ile Ser Lys Leu Met Ala Asn Ser Ala Gly
                645                 650                 655

Ser Val Ala Asp Leu Val Glu Val Gly Ile Arg Val Glu Gly Leu Ala
            660                 665                 670

Asp Val Ile Met Lys Arg Asn Ile Pro Phe Ala Glu Tyr Pro Thr Tyr
        675                 680                 685

Lys Gln Ile Lys Glu Leu Gly Lys Ala Leu Gln Gly Trp Lys Glu Leu
690                 695                 700

Pro Thr Glu Thr Pro Leu Val Ser Ala Tyr Leu Lys Ile Leu Gly Gln
705                 710                 715                 720

Glu Val Ala Phe Ile Asn Ile Asn Lys Glu Leu Leu Gln Gln Val Met
                725                 730                 735

Lys Thr Val Val Glu Pro Ala Asp Arg Asn Ala Ala Ile Lys Arg Ile
            740                 745                 750

Ala Asn Gln Ile Arg Asn Ser Ile Ala Gly Gln Trp Thr Gln Pro Val
        755                 760                 765

Trp Met Gly Glu Leu Arg Tyr Val Val Pro Ser Cys Leu Gly Leu Pro
770                 775                 780

Leu Glu Tyr Gly Ser Tyr Thr Thr Ala Leu Ala Arg Ala Ala Val Ser
785                 790                 795                 800

Val Glu Gly Lys Met Thr Pro Pro Leu Thr Gly Asp Phe Arg Leu Ser
                805                 810                 815

Gln Leu Leu Glu Ser Thr Met Gln Ile Arg Ser Asp Leu Lys Pro Ser
            820                 825                 830

Leu Tyr Val His Thr Val Ala Thr Met Gly Val Asn Thr Glu Tyr Phe
        835                 840                 845

Gln His Ala Val Glu Ile Gln Gly Glu Val Gln Thr Arg Met Pro Met
850                 855                 860

Lys Phe Asp Ala Lys Ile Asp Val Lys Leu Lys Asn Leu Lys Ile Glu
865                 870                 875                 880

```
Thr Asn Pro Cys Arg Glu Glu Thr Glu Ile Val Val Gly Arg His Lys
                885                 890                 895

Ala Phe Ala Val Ser Arg Asn Ile Gly Glu Leu Gly Val Glu Lys Arg
            900                 905                 910

Thr Ser Ile Leu Pro Glu Asp Ala Pro Leu Asp Val Thr Glu Glu Pro
            915                 920                 925

Phe Gln Thr Ser Glu Arg Ala Ser Arg Glu His Phe Ala Met Gln Gly
        930                 935                 940

Pro Asp Ser Met Pro Arg Lys Gln Ser His Ser Ser Arg Glu Asp Leu
945                 950                 955                 960

Arg Arg Ser Thr Gly Lys Arg Ala His Lys Arg Asp Ile Cys Leu Lys
                965                 970                 975

Met His His Ile Gly Cys Gln Leu Cys Phe Ser Arg Arg Ser Arg Asp
            980                 985                 990

Ala Ser Phe Ile Gln Asn Thr Tyr Leu His Lys Leu Ile Gly Glu His
        995                 1000                1005

Glu Ala Lys Ile Val Leu Met Pro Val His Thr Asp Ala Asp Ile
    1010                1015                1020

Asp Lys Ile Gln Leu Glu Ile Gln Ala Gly Ser Arg Ala Ala Ala
    1025                1030                1035

Arg Ile Ile Thr Glu Val Asn Pro Glu Ser Glu Glu Asp Glu
    1040                1045                1050

Ser Ser Pro Tyr Glu Asp Ile Gln Ala Lys Leu Lys Arg Ile Leu
    1055                1060                1065

Gly Ile Asp Ser Met Phe Lys Val Ala Asn Lys Thr Arg His Pro
    1070                1075                1080

Lys Asn Arg Pro Ser Lys Lys Gly Asn Thr Val Leu
    1085                1090                1095

<210> SEQ ID NO 3
<211> LENGTH: 106
<212> TYPE: PRT
<213> ORGANISM: unknown
<220> FEATURE:
<223> OTHER INFORMATION: APV1_CHICK

<400> SEQUENCE: 3

Met Val Gln Tyr Arg Ala Leu Val Ile Ala Val Ile Leu Leu Leu Ser
1               5                   10                  15

Thr Thr Val Pro Glu Val His Ser Lys Ser Ile Ile Asp Arg Glu Arg
            20                  25                  30

Arg Asp Trp Leu Val Ile Pro Asp Ala Ala Ala Tyr Ile Tyr Glu
        35                  40                  45

Ala Val Asn Lys Val Ser Pro Arg Ala Gly Gln Phe Leu Leu Asp Val
    50                  55                  60

Ser Gln Thr Thr Val Val Ser Gly Ile Arg Asn Phe Leu Ile Asn Glu
65                  70                  75                  80

Thr Ala Arg Leu Thr Lys Leu Ala Glu Gln Leu Met Glu Lys Ile Lys
                85                  90                  95

Asn Leu Cys Tyr Thr Lys Val Leu Gly Tyr
            100                 105

<210> SEQ ID NO 4
<211> LENGTH: 147
<212> TYPE: PRT
<213> ORGANISM: unknown
<220> FEATURE:
```

-continued

<223> OTHER INFORMATION: LYC_CHICK

<400> SEQUENCE: 4

```
Met Arg Ser Leu Leu Ile Leu Val Leu Cys Phe Leu Pro Leu Ala Ala
1               5                   10                  15

Leu Gly Lys Val Phe Gly Arg Cys Glu Leu Ala Ala Ala Met Lys Arg
            20                  25                  30

His Gly Leu Asp Asn Tyr Arg Gly Tyr Ser Leu Gly Asn Trp Val Cys
        35                  40                  45

Ala Ala Lys Phe Glu Ser Asn Phe Asn Thr Gln Ala Thr Asn Arg Asn
    50                  55                  60

Thr Asp Gly Ser Thr Asp Tyr Gly Ile Leu Gln Ile Asn Ser Arg Trp
65                  70                  75                  80

Trp Cys Asn Asp Gly Arg Thr Pro Gly Ser Arg Asn Leu Cys Asn Ile
                85                  90                  95

Pro Cys Ser Ala Leu Leu Ser Ser Asp Ile Thr Ala Ser Val Asn Cys
            100                 105                 110

Ala Lys Lys Ile Val Ser Asp Gly Asn Gly Met Asn Ala Trp Val Ala
        115                 120                 125

Trp Arg Asn Arg Cys Lys Gly Thr Asp Val Gln Ala Trp Ile Arg Gly
    130                 135                 140

Cys Arg Leu
145
```

<210> SEQ ID NO 5
<211> LENGTH: 705
<212> TYPE: PRT
<213> ORGANISM: unknown
<220> FEATURE:
<223> OTHER INFORMATION: TRFE_CHICK

<400> SEQUENCE: 5

```
Met Lys Leu Ile Leu Cys Thr Val Leu Ser Leu Gly Ile Ala Ala Val
1               5                   10                  15

Cys Phe Ala Ala Pro Pro Lys Ser Val Ile Arg Trp Cys Thr Ile Ser
            20                  25                  30

Ser Pro Glu Glu Lys Lys Cys Asn Asn Leu Arg Asp Leu Thr Gln Gln
        35                  40                  45

Glu Arg Ile Ser Leu Thr Cys Val Gln Lys Ala Thr Tyr Leu Asp Cys
    50                  55                  60

Ile Lys Ala Ile Ala Asn Asn Glu Ala Asp Ala Ile Ser Leu Asp Gly
65                  70                  75                  80

Gly Gln Ala Phe Glu Ala Gly Leu Ala Pro Tyr Lys Leu Lys Pro Ile
                85                  90                  95

Ala Ala Glu Val Tyr Glu His Thr Glu Gly Ser Thr Thr Ser Tyr Tyr
            100                 105                 110

Ala Val Ala Val Val Lys Lys Gly Thr Glu Phe Thr Val Asn Asp Leu
        115                 120                 125

Gln Gly Lys Thr Ser Cys His Thr Gly Leu Gly Arg Ser Ala Gly Trp
    130                 135                 140

Asn Ile Pro Ile Gly Thr Leu Leu His Arg Gly Ala Ile Glu Trp Glu
145                 150                 155                 160

Gly Ile Glu Ser Gly Ser Val Glu Gln Ala Val Ala Lys Phe Phe Ser
                165                 170                 175

Ala Ser Cys Val Pro Gly Ala Thr Ile Glu Gln Lys Leu Cys Arg Gln
            180                 185                 190
```

```
Cys Lys Gly Asp Pro Lys Thr Lys Cys Ala Arg Asn Ala Pro Tyr Ser
        195                 200                 205

Gly Tyr Ser Gly Ala Phe His Cys Leu Lys Asp Gly Lys Gly Asp Val
        210                 215                 220

Ala Phe Val Lys His Thr Thr Val Asn Glu Asn Ala Pro Asp Gln Lys
225                 230                 235                 240

Asp Glu Tyr Glu Leu Leu Cys Leu Asp Gly Ser Arg Gln Pro Val Asp
                245                 250                 255

Asn Tyr Lys Thr Cys Asn Trp Ala Arg Val Ala Ala His Ala Val Val
                260                 265                 270

Ala Arg Asp Asp Asn Lys Val Glu Asp Ile Trp Ser Phe Leu Ser Lys
        275                 280                 285

Ala Gln Ser Asp Phe Gly Val Asp Thr Lys Ser Asp Phe His Leu Phe
        290                 295                 300

Gly Pro Pro Gly Lys Lys Asp Pro Val Leu Lys Asp Leu Leu Phe Lys
305                 310                 315                 320

Asp Ser Ala Ile Met Leu Lys Arg Val Pro Ser Leu Met Asp Ser Gln
                325                 330                 335

Leu Tyr Leu Gly Phe Glu Tyr Tyr Ser Ala Ile Gln Ser Met Arg Lys
                340                 345                 350

Asp Gln Leu Thr Pro Ser Pro Arg Glu Asn Arg Ile Gln Trp Cys Ala
        355                 360                 365

Val Gly Lys Asp Glu Lys Ser Lys Cys Asp Arg Trp Ser Val Val Ser
        370                 375                 380

Asn Gly Asp Val Glu Cys Thr Val Val Asp Glu Thr Lys Asp Cys Ile
385                 390                 395                 400

Ile Lys Ile Met Lys Gly Glu Ala Asp Ala Val Ala Leu Asp Gly Gly
                405                 410                 415

Leu Val Tyr Thr Ala Gly Val Cys Gly Leu Val Pro Val Met Ala Glu
                420                 425                 430

Arg Tyr Asp Asp Glu Ser Gln Cys Ser Lys Thr Asp Glu Arg Pro Ala
        435                 440                 445

Ser Tyr Phe Ala Val Ala Val Ala Arg Lys Asp Ser Asn Val Asn Trp
        450                 455                 460

Asn Asn Leu Lys Gly Lys Lys Ser Cys His Thr Ala Val Gly Arg Thr
465                 470                 475                 480

Ala Gly Trp Val Ile Pro Met Gly Leu Ile His Asn Arg Thr Gly Thr
                485                 490                 495

Cys Asn Phe Asp Glu Tyr Phe Ser Glu Gly Cys Ala Pro Gly Ser Pro
                500                 505                 510

Pro Asn Ser Arg Leu Cys Gln Leu Cys Gln Gly Ser Gly Gly Ile Pro
        515                 520                 525

Pro Glu Lys Cys Val Ala Ser Ser His Glu Lys Tyr Phe Gly Tyr Thr
        530                 535                 540

Gly Ala Leu Arg Cys Leu Val Glu Lys Gly Asp Val Ala Phe Ile Gln
545                 550                 555                 560

His Ser Thr Val Glu Glu Asn Thr Gly Gly Lys Asn Lys Ala Asp Trp
                565                 570                 575

Ala Lys Asn Leu Gln Met Asp Asp Phe Glu Leu Leu Cys Thr Asp Gly
                580                 585                 590

Arg Arg Ala Asn Val Met Asp Tyr Arg Glu Cys Asn Leu Ala Glu Val
        595                 600                 605

Pro Thr His Ala Val Val Val Arg Pro Glu Lys Ala Asn Lys Ile Arg
610                 615                 620
```

```
Asp Leu Leu Glu Arg Gln Glu Lys Arg Phe Gly Val Asn Gly Ser Glu
625                 630                 635                 640

Lys Ser Lys Phe Met Met Phe Glu Ser Gln Asn Lys Asp Leu Leu Phe
            645                 650                 655

Lys Asp Leu Thr Lys Cys Leu Phe Lys Val Arg Glu Gly Thr Thr Tyr
        660                 665                 670

Lys Glu Phe Leu Gly Asp Lys Phe Tyr Thr Val Ile Ser Ser Leu Lys
    675                 680                 685

Thr Cys Asn Pro Ser Asp Ile Leu Gln Met Cys Ser Phe Leu Glu Gly
        690                 695                 700

Lys
705

<210> SEQ ID NO 6
<211> LENGTH: 2108
<212> TYPE: PRT
<213> ORGANISM: unknown
<220> FEATURE:
<223> OTHER INFORMATION: Q98UI9

<400> SEQUENCE: 6

Met Glu Ile Lys Lys Glu Arg Ser Phe Trp Ile Phe Cys Leu Ile Trp
1               5                   10                  15

Ser Phe Cys Lys Gly Lys Glu Pro Val Gln Ile Val Gln Val Ser Thr
            20                  25                  30

Val Gly Arg Ser Glu Cys Thr Thr Trp Gly Asn Phe His Phe His Thr
        35                  40                  45

Phe Asp His Val Lys Phe Thr Phe Pro Gly Thr Cys Thr Tyr Val Phe
    50                  55                  60

Ala Ser His Cys Asn Asp Ser Tyr Gln Asp Phe Asn Ile Lys Ile Arg
65                  70                  75                  80

Arg Ser Asp Lys Asn Ser His Leu Ile Tyr Phe Thr Val Thr Thr Asp
                85                  90                  95

Gly Val Ile Leu Glu Val Lys Glu Thr Gly Ile Thr Val Asn Gly Asn
            100                 105                 110

Gln Ile Pro Leu Pro Phe Ser Leu Lys Ser Ile Leu Ile Glu Asp Thr
        115                 120                 125

Cys Ala Tyr Phe Gln Val Thr Ser Lys Leu Gly Leu Thr Leu Lys Trp
    130                 135                 140

Asn Trp Ala Asp Thr Leu Leu Leu Asp Leu Glu Glu Thr Tyr Lys Glu
145                 150                 155                 160

Lys Ile Cys Gly Leu Cys Gly Asn Tyr Asp Gly Asn Lys Lys Asn Asp
                165                 170                 175

Leu Ile Leu Asp Gly Tyr Lys Met His Pro Arg Gln Phe Gly Asn Phe
            180                 185                 190

His Lys Val Glu Asp Pro Ser Glu Lys Cys Pro Asp Val Arg Pro Asp
        195                 200                 205

Asp His Thr Gly Arg His Pro Thr Glu Asp Asn Arg Cys Ser Lys
    210                 215                 220

Tyr Lys Lys Met Cys Lys Lys Leu Leu Ser Arg Phe Gly Asn Cys Pro
225                 230                 235                 240

Lys Val Val Ala Phe Asp Asp Tyr Val Ala Thr Cys Thr Glu Asp Met
                245                 250                 255

Cys Asn Cys Val Val Asn Ser Ser Gln Ser Asp Leu Val Ser Ser Cys
            260                 265                 270
```

```
Ile Cys Ser Thr Leu Asn Gln Tyr Ser Arg Asp Cys Val Leu Ser Lys
        275                 280                 285

Gly Asp Pro Gly Glu Trp Arg Thr Lys Glu Leu Cys Tyr Gln Glu Cys
290                 295                 300

Pro Ser Asn Met Glu Tyr Met Glu Cys Gly Asn Ser Cys Ala Asp Thr
305                 310                 315                 320

Cys Ala Asp Pro Glu Arg Ser Lys Ile Cys Lys Ala Pro Cys Thr Asp
                325                 330                 335

Gly Cys Phe Cys Pro Pro Gly Thr Ile Leu Asp Asp Leu Gly Gly Lys
                340                 345                 350

Lys Cys Val Pro Arg Asp Ser Cys Pro Cys Met Phe Gln Gly Lys Val
        355                 360                 365

Tyr Ser Ser Gly Gly Thr Tyr Ser Thr Pro Cys Gln Asn Cys Thr Cys
370                 375                 380

Lys Gly His Trp Ser Cys Ile Ser Leu Pro Cys Ser Gly Ser Cys
385                 390                 395                 400

Ser Ile Asp Gly Gly Phe His Ile Lys Thr Phe Asp Asn Lys Lys Phe
                405                 410                 415

Asn Phe His Gly Asn Cys His Tyr Val Leu Ala Lys Asn Thr Asp Asp
        420                 425                 430

Thr Phe Val Val Ile Gly Glu Ile Ile Gln Cys Gly Thr Ser Lys Thr
            435                 440                 445

Met Thr Cys Leu Lys Asn Val Leu Val Thr Leu Gly Arg Thr Thr Ile
450                 455                 460

Lys Ile Cys Ser Cys Gly Ser Ile Tyr Met Asn Asn Phe Ile Val Lys
465                 470                 475                 480

Leu Pro Val Ser Lys Asp Gly Ile Thr Ile Phe Arg Pro Ser Thr Phe
                485                 490                 495

Phe Ile Lys Ile Leu Ser Ser Ala Gly Val Gln Ile Arg Val Gln Met
            500                 505                 510

Lys Pro Val Met Gln Leu Ser Ile Thr Val Asp His Ser Tyr Gln Asn
        515                 520                 525

Arg Thr Ser Gly Leu Cys Gly Asn Phe Asn Asn Ile Gln Thr Asp Asp
    530                 535                 540

Phe Arg Thr Ala Thr Gly Ala Val Glu Asp Ser Ala Ala Phe Gly
545                 550                 555                 560

Asn Ser Trp Lys Thr Arg Ala Ser Cys Phe Asp Val Glu Asp Ser Phe
                565                 570                 575

Glu Asp Pro Cys Ser Asn Ser Val Asp Lys Glu Lys Phe Ala Gln His
            580                 585                 590

Trp Cys Ala Leu Leu Ser Asn Thr Ser Ser Thr Phe Ala Ala Cys His
        595                 600                 605

Ser Val Val Asp Pro Ser Val Tyr Ile Lys Arg Cys Met Tyr Asp Thr
610                 615                 620

Cys Asn Ala Glu Lys Ser Glu Val Ala Leu Cys Ser Val Leu Ser Thr
625                 630                 635                 640

Tyr Ser Arg Asp Cys Ala Ala Ala Gly Met Thr Leu Lys Gly Trp Arg
                645                 650                 655

Gln Gly Ile Cys Asp Pro Ser Glu Glu Cys Pro Glu Thr Met Val Tyr
        660                 665                 670

Asn Tyr Ser Val Lys Tyr Cys Asn Gln Ser Cys Arg Ser Leu Asp Glu
    675                 680                 685

Pro Asp Pro Leu Cys Lys Val Gln Ile Ala Pro Met Glu Gly Cys Gly
690                 695                 700
```

```
Cys Pro Glu Gly Thr Tyr Leu Asn Asp Glu Glu Cys Val Thr Pro
705                 710                 715                 720

Asp Asp Cys Pro Cys Tyr Tyr Lys Gly Lys Ile Val Gln Pro Gly Asn
            725                 730                 735

Ser Phe Gln Glu Asp Lys Leu Leu Lys Cys Ile Gln Gly Arg Leu
        740                 745                 750

Asp Cys Ile Gly Glu Thr Val Leu Val Lys Asp Cys Pro Ala Pro Met
    755                 760                 765

Tyr Tyr Phe Asn Cys Ser Ser Ala Gly Pro Gly Ala Ile Gly Ser Glu
770                 775                 780

Cys Gln Lys Ser Cys Lys Thr Gln Asp Met His Cys Tyr Val Thr Glu
785                 790                 795                 800

Cys Val Ser Gly Cys Met Cys Pro Asp Gly Leu Val Leu Asp Gly Ser
                805                 810                 815

Gly Gly Cys Ile Pro Lys Asp Gln Cys Pro Cys Val His Gly Gly His
            820                 825                 830

Phe Tyr Lys Pro Gly Glu Thr Ile Arg Val Asp Cys Asn Thr Cys Thr
        835                 840                 845

Cys Asn Lys Arg Gln Trp Asn Cys Thr Asp Asn Pro Cys Lys Gly Thr
850                 855                 860

Cys Thr Val Tyr Gly Asn Gly His Tyr Met Ser Phe Asp Gly Glu Lys
865                 870                 875                 880

Phe Asp Phe Leu Gly Asp Cys Asp Tyr Ile Leu Ala Gln Asp Phe Cys
                885                 890                 895

Pro Asn Asn Met Asp Ala Gly Thr Phe Arg Ile Val Ile Gln Asn Asn
            900                 905                 910

Ala Cys Gly Lys Ser Leu Ser Ile Cys Ser Leu Lys Ile Thr Leu Ile
        915                 920                 925

Phe Glu Ser Ser Glu Ile Arg Leu Leu Glu Gly Arg Ile Gln Glu Ile
930                 935                 940

Ala Thr Asp Pro Gly Ala Glu Lys Asn Tyr Lys Val Asp Leu Arg Gly
945                 950                 955                 960

Gly Tyr Ile Val Ile Glu Thr Thr Gln Gly Met Ser Phe Met Trp Asp
                965                 970                 975

Gln Lys Thr Thr Val Val His Val Thr Pro Ser Phe Gln Gly Lys
            980                 985                 990

Val Cys Gly Leu Cys Gly Asp Phe Asp Gly Arg Ser Arg Asn Asp Phe
        995                 1000                1005

Thr Thr Arg Gly Gln Ser Val Glu Met Ser Ile Gln Glu Phe Gly
1010                1015                1020

Asn Ser Trp Lys Ile Thr Ser Thr Cys Ser Asn Ile Asn Met Thr
    1025                1030                1035

Asp Leu Cys Ala Asp Gln Pro Phe Lys Ser Ala Leu Gly Gln Lys
    1040                1045                1050

His Cys Ser Ile Ile Lys Ser Ser Val Phe Glu Ala Cys His Ser
    1055                1060                1065

Lys Val Asn Pro Ile Pro Tyr Tyr Glu Ser Cys Val Ser Asp Phe
    1070                1075                1080

Cys Gly Cys Asp Ser Val Gly Asp Cys Glu Cys Phe Cys Thr Ser
    1085                1090                1095

Val Ala Ala Tyr Ala Arg Ser Cys Ser Thr Ala Gly Val Cys Ile
    1100                1105                1110
```

-continued

```
Asn Trp Arg Thr Pro Ala Ile Cys Pro Val Phe Cys Asp Tyr Tyr
1115                1120                1125

Asn Pro Pro Asp Lys His Glu Trp Phe Tyr Lys Pro Cys Gly Ala
1130                1135                1140

Pro Cys Leu Lys Thr Cys Arg Asn Pro Gln Gly Lys Cys Gly Asn
1145                1150                1155

Ile Leu Tyr Ser Leu Glu Gly Cys Tyr Pro Glu Cys Ser Pro Asp
1160                1165                1170

Lys Pro Tyr Phe Asp Glu Glu Arg Arg Glu Cys Val Ser Leu Pro
1175                1180                1185

Asp Cys Thr Ser Cys Asn Pro Glu Glu Lys Leu Cys Thr Glu Asp
1190                1195                1200

Ser Lys Asp Cys Leu Cys Tyr Asn Gly Lys Thr Tyr Pro Leu
1205                1210                1215

Asn Glu Thr Ile Tyr Ser Gln Thr Glu Gly Thr Lys Cys Gly Asn
1220                1225                1230

Ala Phe Cys Gly Pro Asn Gly Met Ile Ile Glu Thr Phe Ile Pro
1235                1240                1245

Cys Ser Thr Leu Ser Val Pro Ala Gln Glu Gln Leu Met Gln Pro
1250                1255                1260

Val Thr Ser Ala Pro Leu Leu Ser Thr Glu Ala Thr Pro Cys Phe
1265                1270                1275

Cys Thr Asp Asn Gly Gln Leu Ile Gln Met Gly Glu Asn Val Ser
1280                1285                1290

Leu Pro Met Asn Ile Ser Gly His Cys Ala Tyr Ser Ile Cys Asn
1295                1300                1305

Ala Ser Cys Gln Ile Glu Leu Ile Trp Ala Glu Cys Lys Val Val
1310                1315                1320

Gln Thr Glu Ala Leu Glu Thr Cys Glu Pro Asn Ser Glu Ala Cys
1325                1330                1335

Pro Pro Thr Ala Ala Pro Asn Ala Thr Ser Leu Val Pro Ala Thr
1340                1345                1350

Ala Leu Ala Pro Met Ser Asp Cys Leu Gly Leu Ile Pro Pro Arg
1355                1360                1365

Lys Phe Asn Glu Ser Trp Asp Phe Gly Asn Cys Gln Ile Ala Thr
1370                1375                1380

Cys Leu Gly Glu Glu Asn Asn Ile Lys Leu Ser Ser Ile Thr Cys
1385                1390                1395

Pro Pro Gln Gln Leu Lys Leu Cys Val Asn Gly Phe Pro Phe Met
1400                1405                1410

Lys His His Asp Glu Thr Gly Cys Cys Glu Val Phe Glu Cys Gln
1415                1420                1425

Cys Ile Cys Ser Gly Trp Gly Asn Glu His Tyr Val Thr Phe Asp
1430                1435                1440

Gly Thr Tyr Tyr His Phe Lys Glu Asn Cys Thr Tyr Val Leu Val
1445                1450                1455

Glu Leu Ile Gln Pro Ser Ser Glu Lys Phe Trp Ile His Ile Asp
1460                1465                1470

Asn Tyr Tyr Cys Gly Ala Ala Asp Gly Ala Ile Cys Ser Met Ser
1475                1480                1485

Leu Leu Ile Phe His Ser Asn Ser Leu Val Ile Leu Thr Gln Ala
1490                1495                1500

Lys Glu His Gly Lys Gly Thr Asn Leu Val Leu Phe Asn Asp Lys
1505                1510                1515
```

```
Lys Val Val Pro Asp Ile Ser Lys Asn Gly Ile Arg Ile Thr Ser
    1520            1525                1530

Ser Gly Leu Tyr Ile Ile Val Glu Ile Pro Glu Leu Glu Val Tyr
    1535            1540                1545

Val Ser Tyr Ser Arg Leu Ala Phe Tyr Ile Lys Leu Pro Phe Gly
    1550            1555                1560

Lys Tyr Tyr Asn Asn Thr Met Gly Leu Cys Gly Thr Cys Thr Asn
    1565            1570                1575

Gln Lys Ser Asp Asp Ala Arg Lys Arg Asn Gly Glu Val Thr Asp
    1580            1585                1590

Ser Phe Lys Glu Met Ala Leu Asp Trp Lys Ala Pro Val Ser Thr
    1595            1600                1605

Asn Arg Tyr Cys Asn Pro Gly Ile Ser Glu Pro Val Lys Ile Glu
    1610            1615                1620

Asn Tyr Gln His Cys Glu Pro Ser Glu Leu Cys Lys Ile Ile Trp
    1625            1630                1635

Asn Leu Thr Glu Cys His Arg Val Val Pro Pro Gln Pro Tyr Tyr
    1640            1645                1650

Glu Ala Cys Val Ala Ser Arg Cys Ser Gln Gln His Pro Ser Thr
    1655            1660                1665

Glu Cys Gln Ser Met Gln Thr Tyr Ala Ala Leu Cys Gly Leu His
    1670            1675                1680

Gly Ile Cys Val Asp Trp Arg Gly Gln Thr Asn Gly Gln Cys Glu
    1685            1690                1695

Ala Thr Cys Ala Arg Asp Gln Val Tyr Lys Pro Cys Gly Glu Ala
    1700            1705                1710

Lys Arg Asn Thr Cys Phe Ser Arg Glu Val Ile Val Asp Thr Leu
    1715            1720                1725

Leu Ser Arg Asn Asn Thr Pro Val Phe Val Glu Gly Cys Tyr Cys
    1730            1735                1740

Pro Asp Gly Asn Ile Leu Leu Asn Glu His Asp Gly Ile Cys Val
    1745            1750                1755

Ser Val Cys Gly Cys Thr Ala Gln Asp Gly Ser Val Lys Lys Pro
    1760            1765                1770

Arg Glu Ala Trp Glu His Asp Cys Gln Tyr Cys Thr Cys Asp Glu
    1775            1780                1785

Glu Thr Leu Asn Ile Ser Cys Phe Pro Arg Pro Cys Ala Lys Ser
    1790            1795                1800

Pro Pro Ile Asn Cys Thr Lys Glu Gly Phe Val Arg Lys Ile Lys
    1805            1810                1815

Pro Arg Leu Asp Asp Pro Cys Cys Thr Glu Thr Val Cys Glu Cys
    1820            1825                1830

Asp Ile Lys Thr Cys Ile Ile Asn Lys Thr Ala Cys Asp Leu Gly
    1835            1840                1845

Phe Gln Pro Val Val Ala Ile Ser Glu Asp Gly Cys Cys Pro Ile
    1850            1855                1860

Phe Ser Cys Ile Pro Lys Gly Val Cys Val Ser Glu Gly Val Glu
    1865            1870                1875

Phe Lys Pro Gly Ala Val Val Pro Lys Ser Ser Cys Glu Asp Cys
    1880            1885                1890

Val Cys Thr Asp Glu Gln Asp Ala Val Thr Gly Thr Asn Arg Ile
    1895            1900                1905
```

-continued

```
Gln Cys Val Pro Val Lys Cys Gln Thr Thr Cys Gln Gln Gly Phe
    1910                1915                1920

Arg Tyr Val Glu Lys Glu Gly Gln Cys Cys Ser Gln Cys Gln Gln
    1925                1930                1935

Val Ala Cys Val Ala Asn Phe Pro Phe Gly Ser Val Thr Ile Glu
    1940                1945                1950

Val Gly Lys Ser Tyr Lys Ala Pro Tyr Asp Asn Cys Thr Gln Tyr
    1955                1960                1965

Thr Cys Thr Glu Ser Gly Gly Gln Phe Ser Leu Thr Ser Thr Val
    1970                1975                1980

Lys Val Cys Leu Pro Phe Glu Glu Ser Asn Cys Val Pro Gly Thr
    1985                1990                1995

Val Asp Val Thr Ser Asp Gly Cys Cys Lys Thr Cys Ile Asp Leu
    2000                2005                2010

Pro His Lys Cys Lys Arg Ser Met Lys Glu Gln Tyr Ile Val His
    2015                2020                2025

Lys His Cys Lys Ser Ala Ala Pro Val Pro Val Pro Phe Cys Glu
    2030                2035                2040

Gly Thr Cys Ser Thr Tyr Ser Val Tyr Ser Phe Glu Asn Asn Glu
    2045                2050                2055

Met Glu His Lys Cys Ile Cys Cys His Glu Lys Lys Ser His Val
    2060                2065                2070

Glu Lys Val Glu Leu Val Cys Ser Glu His Lys Thr Leu Lys Phe
    2075                2080                2085

Ser Tyr Val His Val Asp Glu Cys Gly Cys Val Glu Thr Lys Cys
    2090                2095                2100

Pro Met Arg Arg Thr
    2105

<210> SEQ ID NO 7
<211> LENGTH: 1124
<212> TYPE: PRT
<213> ORGANISM: unknown
<220> FEATURE:
<223> OTHER INFORMATION: VIT1_CHICK

<400> SEQUENCE: 7

Gln His Leu Asn Tyr Gln Pro Asp Phe Gly Glu Asn Lys Val Tyr Thr
1               5                   10                  15

Tyr Asn Tyr Glu Ser Ile Leu Phe Ser Gly Ile Pro Glu Lys Gly Leu
            20                  25                  30

Ala Arg Thr Gly Ile Arg Ile Arg Ser Glu Val Glu Ile Ser Gly Ile
        35                  40                  45

Gly Pro Lys Leu Cys Leu Ile Arg Ile His Ser Ile Glu Ala Ala Glu
    50                  55                  60

Tyr Asn Gly Ile Trp Pro Thr Ser Ser Phe Ser Arg Ser Leu Lys Leu
65                  70                  75                  80

Thr Gln Ala Leu Thr Gly Gln Leu Ser Ile Pro Ile Lys Phe Glu Tyr
                85                  90                  95

Ser Asn Gly His Val Gly Asn Leu Met Ala Pro Asp Ser Val Ser Asp
            100                 105                 110

Asp Gly Leu Asn Ile Tyr Arg Gly Ile Leu Asn Ile Leu Glu Leu Ser
        115                 120                 125

Leu Lys Lys Met Gln His Ser Tyr Ser Ile Gln Glu Ala Gly Ile Gly
    130                 135                 140
```

-continued

```
Gly Ile Cys Asn Thr Thr Tyr Ala Ile Gln Glu Asn Lys Lys Ala Asn
145                 150                 155                 160

Leu Val Asp Val Thr Lys Ser Lys Asp Leu Asn Ser Cys Glu Glu Lys
                165                 170                 175

Val Gln Val Thr Gly Ser Ala Tyr Thr Gln Pro Cys Gln Thr Cys
            180                 185                 190

Gln Gln Arg Asn Lys Asn Ser Arg Ala Thr Ala Thr Tyr Asn Tyr Lys
        195                 200                 205

Ile Lys Tyr Thr His Asn Glu Ala Val Ile Thr Gln Ala Glu Val Glu
    210                 215                 220

Glu Val His Gln Phe Thr Pro Phe His Glu Ile Thr Gly Gly Asn Ala
225                 230                 235                 240

Ile Val Glu Ala Arg Gln Lys Leu Ala Leu Ile Glu Val Gln Lys Gln
                245                 250                 255

Val Ala Glu Val Pro Pro Lys Glu Phe Gln Lys Arg Gly Ser Leu Gln
            260                 265                 270

Tyr Gln Phe Gly Ser Glu Leu Leu Gln Leu Pro Val His Leu Phe Lys
        275                 280                 285

Ile Lys Asp Val Glu Arg Gln Ile Glu Arg Leu Gln Asp Leu Val
    290                 295                 300

Glu Thr Thr Tyr Glu Gln Leu Pro Ser Asp Ala Pro Ala Lys Ala Leu
305                 310                 315                 320

Lys Leu Met His Leu Leu Arg Ala Ala Asn Glu Asn Tyr Glu Ser
                325                 330                 335

Val Trp Lys Gln Phe Ser Ser Arg Pro Ala Tyr Arg Arg Tyr Leu Leu
            340                 345                 350

Asp Leu Leu Pro Ala Ala Ala Ser His Arg Ser Leu Arg Phe Leu Arg
        355                 360                 365

His Lys Met Glu Arg Gln Glu Leu Thr Asn Trp Glu Ile Ala Gln Thr
    370                 375                 380

Val Leu Val Ala Leu His Ser Ser Ser Pro Thr Gln Glu Val Met Glu
385                 390                 395                 400

Glu Ala Thr Leu Ile Val Lys Lys His Cys Pro Arg Ser Ser Ser Val
                405                 410                 415

Leu Arg Lys Val Cys Leu Leu Ser Tyr Ala Ser Leu Cys His Lys Arg
            420                 425                 430

Cys Ser Ser Pro Tyr Ser Cys Ser Glu Cys Leu Gln Val Phe His Val
        435                 440                 445

Phe Ala Gly Glu Ala Leu Gly Lys Ser Asn Ile Glu Val Leu Leu
    450                 455                 460

Ala Leu Lys Ala Leu Gly Asn Val Gly His Pro Ala Ser Ile Lys His
465                 470                 475                 480

Ile Lys Lys Phe Leu Pro Gly Tyr Ala Ala Gly Ala Ser Glu Leu Pro
                485                 490                 495

Leu Lys Val His Glu Thr Ala Val Met Ala Leu Lys Ser Ile Gly Met
            500                 505                 510

Arg Asp Pro Gln Met Val Gln Ala Ile Thr Leu Glu Ile Phe Leu Asn
        515                 520                 525

His Lys Ile His Pro Arg Ile Arg Met Leu Ala Ala Val Val Leu Leu
    530                 535                 540

Glu Thr Lys Pro Gly Leu Pro Ile Leu Met Ile Leu Val Asp Ala Val
545                 550                 555                 560

Leu Lys Glu Pro Ser Met Gln Val Ala Ser Phe Ile Tyr Ser His Leu
                565                 570                 575
```

```
Arg Ala Leu Gly Arg Ser Thr Ala Pro Asp Leu Gln Met Met Ala Ser
            580                 585                 590

Ala Cys Arg Met Ala Val Arg Ala Leu Ser Pro Lys Phe Asp Arg Ser
        595                 600                 605

Gly Tyr Gln Phe Ser Lys Val Phe Arg Phe Ser Met Phe Lys Glu Phe
    610                 615                 620

Leu Met Ser Gly Leu Ala Ala Lys Tyr Phe Val Leu Asn Asn Ala Gly
625                 630                 635                 640

Ser Leu Ile Pro Thr Met Ala Val Ser Gln Leu Arg Thr His Phe Leu
                645                 650                 655

Gly Arg Val Ala Asp Pro Ile Glu Val Gly Ile Ala Ala Glu Gly Leu
            660                 665                 670

Gln Glu Met Phe Val Arg Gly Tyr Ser Pro Asp Lys Asp Trp Glu Thr
        675                 680                 685

Asn Tyr Asp Phe Arg Glu Ile Leu Lys Lys Leu Ser Asp Trp Lys Ala
    690                 695                 700

Leu Pro Arg Asp Lys Pro Phe Ala Ser Gly Tyr Leu Lys Met Phe Gly
705                 710                 715                 720

Gln Glu Leu Leu Phe Gly Arg Leu Asp Lys Asp Thr Leu Gln Asn Val
                725                 730                 735

Leu Gln Val Trp Tyr Gly Pro Asp Glu Lys Ile Pro Ser Ile Arg Arg
            740                 745                 750

Leu Ile Ser Ser Leu Gln Thr Gly Ile Gly Arg Gln Trp Thr Lys Ala
        755                 760                 765

Leu Leu Leu Ser Glu Ile Arg Cys Ile Val Pro Thr Cys Val Gly Phe
    770                 775                 780

Pro Met Glu Thr Ser Phe Tyr Tyr Ser Ser Val Thr Lys Val Ala Gly
785                 790                 795                 800

Asn Val Gln Ala Gln Ile Thr Pro Ser Pro Arg Ser Asp Phe Arg Leu
                805                 810                 815

Thr Glu Leu Leu Asn Ser Asn Val Arg Leu Arg Ser Lys Met Ser Leu
            820                 825                 830

Ser Met Ala Lys His Met Thr Phe Val Ile Gly Ile Asn Thr Asn Met
        835                 840                 845

Ile Gln Ala Gly Leu Glu Ala His Thr Lys Val Asn Ala His Val Pro
    850                 855                 860

Val Asn Val Val Ala Thr Ile Gln Met Lys Glu Lys Ser Ile Lys Ala
865                 870                 875                 880

Glu Ile Pro Pro Cys Lys Glu Thr Asn Leu Ile Ile Val Ser Ser
                885                 890                 895

Lys Thr Phe Ala Val Thr Arg Asn Ile Glu Asp Leu Ala Ala Ser Lys
            900                 905                 910

Met Thr Pro Val Leu Leu Pro Glu Ala Val Pro Asp Ile Met Lys Met
        915                 920                 925

Ser Phe Asp Ser Asp Ser Ala Ser Gly Glu Thr Asp Asn Ile Arg Asp
    930                 935                 940

Arg Gln Ser Val Glu Asp Val Ser Ser Gly Asn Ser Phe Ser Phe Gly
945                 950                 955                 960

His Pro Ser Ser Gly Lys Glu Pro Phe Ile Gln Ser Met Cys Ser Asn
                965                 970                 975

Ala Ser Thr Phe Gly Val Gln Val Cys Ile Glu Lys Lys Ser Val His
            980                 985                 990
```

-continued

```
Ala Ala Phe Ile Arg Asn Val Pro Leu Tyr Asn Ala Ile Gly Glu His
        995                 1000                1005

Ala Leu Arg Met Ser Phe Lys Pro Val Tyr Ser Asp Val Pro Ile
    1010                1015                1020

Glu Lys Ile Gln Val Thr Ile Gln Ala Gly Asp Gln Ala Pro Thr
    1025                1030                1035

Lys Met Val Arg Leu Val Thr Phe Glu Asp Pro Glu Arg Gln Glu
    1040                1045                1050

Ser Ser Arg Lys Glu Val Met Lys Arg Val Lys Lys Ile Leu Asp
    1055                1060                1065

Asp Thr Asp Asn Gln Ala Thr Arg Asn Ser Arg Ser Ser Ser Ser
    1070                1075                1080

Ser Ala Ser Ser Ile Ser Glu Ser Ser Glu Ser Thr Thr Ser Thr
    1085                1090                1095

Pro Ser Ser Ser Asp Ser Asp Asn Arg Ala Ser Gln Gly Asp Pro
    1100                1105                1110

Gln Ile Asn Leu Lys Ser Arg Gln Ser Lys Ala
    1115                1120

<210> SEQ ID NO 8
<211> LENGTH: 385
<212> TYPE: PRT
<213> ORGANISM: unknown
<220> FEATURE:
<223> OTHER INFORMATION: OVAL_CHICK

<400> SEQUENCE: 8

Gly Ser Ile Gly Ala Ala Ser Met Glu Phe Cys Phe Asp Val Phe Lys
1               5                   10                  15

Glu Leu Lys Val His His Ala Asn Glu Asn Ile Phe Tyr Cys Pro Ile
            20                  25                  30

Ala Ile Met Ser Ala Leu Ala Met Val Tyr Leu Gly Ala Lys Asp Ser
        35                  40                  45

Thr Arg Thr Gln Ile Asn Lys Val Val Arg Phe Asp Lys Leu Pro Gly
    50                  55                  60

Phe Gly Asp Ser Ile Glu Ala Gln Cys Gly Thr Ser Val Asn Val His
65                  70                  75                  80

Ser Ser Leu Arg Asp Ile Leu Asn Gln Ile Thr Lys Pro Asn Asp Val
                85                  90                  95

Tyr Ser Phe Ser Leu Ala Ser Arg Leu Tyr Ala Glu Glu Arg Tyr Pro
            100                 105                 110

Ile Leu Pro Glu Tyr Leu Gln Cys Val Lys Glu Leu Tyr Arg Gly Gly
        115                 120                 125

Leu Glu Pro Ile Asn Phe Gln Thr Ala Ala Asp Gln Ala Arg Glu Leu
    130                 135                 140

Ile Asn Ser Trp Val Glu Ser Gln Thr Asn Gly Ile Ile Arg Asn Val
145                 150                 155                 160

Leu Gln Pro Ser Ser Val Asp Ser Gln Thr Ala Met Val Leu Val Asn
                165                 170                 175

Ala Ile Val Phe Lys Gly Leu Trp Glu Lys Ala Phe Lys Asp Glu Asp
            180                 185                 190

Thr Gln Ala Met Pro Phe Arg Val Thr Glu Gln Glu Ser Lys Pro Val
        195                 200                 205

Gln Met Met Tyr Gln Ile Gly Leu Phe Arg Val Ala Ser Met Ala Ser
    210                 215                 220
```

Glu Lys Met Lys Ile Leu Glu Leu Pro Phe Ala Ser Gly Thr Met Ser
225                 230                 235                 240

Met Leu Val Leu Leu Pro Asp Glu Val Ser Gly Leu Glu Gln Leu Glu
            245                 250                 255

Ser Ile Ile Asn Phe Glu Lys Leu Thr Glu Trp Thr Ser Ser Asn Val
        260                 265                 270

Met Glu Glu Arg Lys Ile Lys Val Tyr Leu Pro Arg Met Lys Met Glu
    275                 280                 285

Glu Lys Tyr Asn Leu Thr Ser Val Leu Met Ala Met Gly Ile Thr Asp
290                 295                 300

Val Phe Ser Ser Ser Ala Asn Leu Ser Gly Ile Ser Ser Ala Glu Ser
305                 310                 315                 320

Leu Lys Ile Ser Gln Ala Val His Ala Ala His Ala Glu Ile Asn Glu
            325                 330                 335

Ala Gly Arg Glu Val Val Gly Ser Ala Glu Ala Gly Val Asp Ala Ala
        340                 345                 350

Ser Val Ser Glu Glu Phe Arg Ala Asp His Pro Phe Leu Phe Cys Ile
    355                 360                 365

Lys His Ile Ala Thr Asn Ala Val Leu Phe Phe Gly Arg Cys Val Ser
370                 375                 380

Pro
385

<210> SEQ ID NO 9
<211> LENGTH: 2108
<212> TYPE: PRT
<213> ORGANISM: unknown
<220> FEATURE:
<223> OTHER INFORMATION: Q98UI9

<400> SEQUENCE: 9

Met Glu Ile Lys Lys Glu Arg Ser Phe Trp Ile Phe Cys Leu Ile Trp
1               5                   10                  15

Ser Phe Cys Lys Gly Lys Glu Pro Val Gln Ile Val Gln Val Ser Thr
            20                  25                  30

Val Gly Arg Ser Glu Cys Thr Thr Trp Gly Asn Phe His Phe His Thr
        35                  40                  45

Phe Asp His Val Lys Phe Thr Phe Pro Gly Thr Cys Thr Tyr Val Phe
    50                  55                  60

Ala Ser His Cys Asn Asp Ser Tyr Gln Asp Phe Asn Ile Lys Ile Arg
65                  70                  75                  80

Arg Ser Asp Lys Asn Ser His Leu Ile Tyr Phe Thr Val Thr Thr Asp
                85                  90                  95

Gly Val Ile Leu Glu Val Lys Glu Thr Gly Ile Thr Val Asn Gly Asn
            100                 105                 110

Gln Ile Pro Leu Pro Phe Ser Leu Lys Ser Ile Leu Ile Glu Asp Thr
        115                 120                 125

Cys Ala Tyr Phe Gln Val Thr Ser Lys Leu Gly Leu Thr Leu Lys Trp
    130                 135                 140

Asn Trp Ala Asp Thr Leu Leu Leu Asp Leu Glu Glu Thr Tyr Lys Glu
145                 150                 155                 160

Lys Ile Cys Gly Leu Cys Gly Asn Tyr Asp Gly Asn Lys Lys Asn Asp
                165                 170                 175

Leu Ile Leu Asp Gly Tyr Lys Met His Pro Arg Gln Phe Gly Asn Phe
            180                 185                 190

-continued

His Lys Val Glu Asp Pro Ser Glu Lys Cys Pro Asp Val Arg Pro Asp
        195                 200                 205

Asp His Thr Gly Arg His Pro Thr Glu Asp Asp Asn Arg Cys Ser Lys
    210                 215                 220

Tyr Lys Lys Met Cys Lys Lys Leu Leu Ser Arg Phe Gly Asn Cys Pro
225                 230                 235                 240

Lys Val Val Ala Phe Asp Asp Tyr Val Ala Thr Cys Thr Glu Asp Met
                245                 250                 255

Cys Asn Cys Val Val Asn Ser Ser Gln Ser Asp Leu Val Ser Ser Cys
            260                 265                 270

Ile Cys Ser Thr Leu Asn Gln Tyr Ser Arg Asp Cys Val Leu Ser Lys
        275                 280                 285

Gly Asp Pro Gly Glu Trp Arg Thr Lys Glu Leu Cys Tyr Gln Glu Cys
290                 295                 300

Pro Ser Asn Met Glu Tyr Met Glu Cys Gly Asn Ser Cys Ala Asp Thr
305                 310                 315                 320

Cys Ala Asp Pro Glu Arg Ser Lys Ile Cys Lys Ala Pro Cys Thr Asp
                325                 330                 335

Gly Cys Phe Cys Pro Pro Gly Thr Ile Leu Asp Asp Leu Gly Gly Lys
            340                 345                 350

Lys Cys Val Pro Arg Asp Ser Cys Pro Cys Met Phe Gln Gly Lys Val
        355                 360                 365

Tyr Ser Ser Gly Gly Thr Tyr Ser Thr Pro Cys Gln Asn Cys Thr Cys
    370                 375                 380

Lys Gly His Trp Ser Cys Ile Ser Leu Pro Cys Ser Gly Ser Cys
385                 390                 395                 400

Ser Ile Asp Gly Gly Phe His Ile Lys Thr Phe Asp Asn Lys Lys Phe
                405                 410                 415

Asn Phe His Gly Asn Cys His Tyr Val Leu Ala Lys Asn Thr Asp Asp
            420                 425                 430

Thr Phe Val Val Ile Gly Glu Ile Gln Cys Gly Thr Ser Lys Thr
        435                 440                 445

Met Thr Cys Leu Lys Asn Val Leu Val Thr Leu Gly Arg Thr Thr Ile
450                 455                 460

Lys Ile Cys Ser Cys Gly Ser Ile Tyr Met Asn Asn Phe Ile Val Lys
465                 470                 475                 480

Leu Pro Val Ser Lys Asp Gly Ile Thr Ile Phe Arg Pro Ser Thr Phe
                485                 490                 495

Phe Ile Lys Ile Leu Ser Ser Ala Gly Val Gln Ile Arg Val Gln Met
            500                 505                 510

Lys Pro Val Met Gln Leu Ser Ile Thr Val Asp His Ser Tyr Gln Asn
        515                 520                 525

Arg Thr Ser Gly Leu Cys Gly Asn Phe Asn Asn Ile Gln Thr Asp Asp
    530                 535                 540

Phe Arg Thr Ala Thr Gly Ala Val Glu Asp Ser Ala Ala Ala Phe Gly
545                 550                 555                 560

Asn Ser Trp Lys Thr Arg Ala Ser Cys Phe Asp Val Glu Asp Ser Phe
                565                 570                 575

Glu Asp Pro Cys Ser Asn Ser Val Asp Lys Glu Lys Phe Ala Gln His
            580                 585                 590

Trp Cys Ala Leu Leu Ser Asn Thr Ser Ser Thr Phe Ala Ala Cys His
        595                 600                 605

Ser Val Val Asp Pro Ser Val Tyr Ile Lys Arg Cys Met Tyr Asp Thr
    610                 615                 620

```
Cys Asn Ala Glu Lys Ser Glu Val Ala Leu Cys Ser Val Leu Ser Thr
625                 630                 635                 640

Tyr Ser Arg Asp Cys Ala Ala Gly Met Thr Leu Lys Gly Trp Arg
            645                 650                 655

Gln Gly Ile Cys Asp Pro Ser Glu Glu Cys Pro Glu Thr Met Val Tyr
            660                 665                 670

Asn Tyr Ser Val Lys Tyr Cys Asn Gln Ser Cys Arg Ser Leu Asp Glu
            675                 680                 685

Pro Asp Pro Leu Cys Lys Val Gln Ile Ala Pro Met Glu Gly Cys Gly
            690                 695                 700

Cys Pro Glu Gly Thr Tyr Leu Asn Asp Glu Glu Cys Val Thr Pro
705                 710                 715                 720

Asp Asp Cys Pro Cys Tyr Tyr Lys Gly Lys Ile Val Gln Pro Gly Asn
            725                 730                 735

Ser Phe Gln Glu Asp Lys Leu Leu Cys Lys Cys Ile Gln Gly Arg Leu
            740                 745                 750

Asp Cys Ile Gly Glu Thr Val Leu Val Lys Asp Cys Pro Ala Pro Met
            755                 760                 765

Tyr Tyr Phe Asn Cys Ser Ser Ala Gly Pro Gly Ala Ile Gly Ser Glu
            770                 775                 780

Cys Gln Lys Ser Cys Lys Thr Gln Asp Met His Cys Tyr Val Thr Glu
785                 790                 795                 800

Cys Val Ser Gly Cys Met Cys Pro Asp Gly Leu Val Leu Asp Gly Ser
                805                 810                 815

Gly Gly Cys Ile Pro Lys Asp Gln Cys Pro Cys Val His Gly Gly His
            820                 825                 830

Phe Tyr Lys Pro Gly Glu Thr Ile Arg Val Asp Cys Asn Thr Cys Thr
            835                 840                 845

Cys Asn Lys Arg Gln Trp Asn Cys Thr Asp Asn Pro Cys Lys Gly Thr
850                 855                 860

Cys Thr Val Tyr Gly Asn Gly His Tyr Met Ser Phe Asp Gly Glu Lys
865                 870                 875                 880

Phe Asp Phe Leu Gly Asp Cys Asp Tyr Ile Leu Ala Gln Asp Phe Cys
                885                 890                 895

Pro Asn Asn Met Asp Ala Gly Thr Phe Arg Ile Val Ile Gln Asn Asn
            900                 905                 910

Ala Cys Gly Lys Ser Leu Ser Ile Cys Ser Leu Lys Ile Thr Leu Ile
            915                 920                 925

Phe Glu Ser Ser Glu Ile Arg Leu Leu Glu Gly Arg Ile Gln Glu Ile
930                 935                 940

Ala Thr Asp Pro Gly Ala Glu Lys Asn Tyr Lys Val Asp Leu Arg Gly
945                 950                 955                 960

Gly Tyr Ile Val Ile Glu Thr Thr Gln Gly Met Ser Phe Met Trp Asp
                965                 970                 975

Gln Lys Thr Thr Val Val Val His Val Thr Pro Ser Phe Gln Gly Lys
            980                 985                 990

Val Cys Gly Leu Cys Gly Asp Phe Asp Gly Arg Ser Arg Asn Asp Phe
            995                 1000                1005

Thr Thr Arg Gly Gln Ser Val Glu Met Ser Ile Gln Glu Phe Gly
    1010                1015                1020

Asn Ser Trp Lys Ile Thr Ser Thr Cys Ser Asn Ile Asn Met Thr
    1025                1030                1035
```

-continued

```
Asp Leu Cys Ala Asp Gln Pro Phe Lys Ser Ala Leu Gly Gln Lys
1040                1045                1050

His Cys Ser Ile Ile Lys Ser Ser Val Phe Glu Ala Cys His Ser
1055                1060                1065

Lys Val Asn Pro Ile Pro Tyr Tyr Glu Ser Cys Val Ser Asp Phe
1070                1075                1080

Cys Gly Cys Asp Ser Val Gly Asp Cys Glu Cys Phe Cys Thr Ser
1085                1090                1095

Val Ala Ala Tyr Ala Arg Ser Cys Ser Thr Ala Gly Val Cys Ile
1100                1105                1110

Asn Trp Arg Thr Pro Ala Ile Cys Pro Val Phe Cys Asp Tyr Tyr
1115                1120                1125

Asn Pro Pro Asp Lys His Glu Trp Phe Tyr Lys Pro Cys Gly Ala
1130                1135                1140

Pro Cys Leu Lys Thr Cys Arg Asn Pro Gln Gly Lys Cys Gly Asn
1145                1150                1155

Ile Leu Tyr Ser Leu Glu Gly Cys Tyr Pro Glu Cys Ser Pro Asp
1160                1165                1170

Lys Pro Tyr Phe Asp Glu Glu Arg Arg Glu Cys Val Ser Leu Pro
1175                1180                1185

Asp Cys Thr Ser Cys Asn Pro Glu Glu Lys Leu Cys Thr Glu Asp
1190                1195                1200

Ser Lys Asp Cys Leu Cys Cys Tyr Asn Gly Lys Thr Tyr Pro Leu
1205                1210                1215

Asn Glu Thr Ile Tyr Ser Gln Thr Glu Gly Thr Lys Cys Gly Asn
1220                1225                1230

Ala Phe Cys Gly Pro Asn Gly Met Ile Ile Glu Thr Phe Ile Pro
1235                1240                1245

Cys Ser Thr Leu Ser Val Pro Ala Gln Glu Gln Leu Met Gln Pro
1250                1255                1260

Val Thr Ser Ala Pro Leu Leu Ser Thr Glu Ala Thr Pro Cys Phe
1265                1270                1275

Cys Thr Asp Asn Gly Gln Leu Ile Gln Met Gly Glu Asn Val Ser
1280                1285                1290

Leu Pro Met Asn Ile Ser Gly His Cys Ala Tyr Ser Ile Cys Asn
1295                1300                1305

Ala Ser Cys Gln Ile Glu Leu Ile Trp Ala Glu Cys Lys Val Val
1310                1315                1320

Gln Thr Glu Ala Leu Glu Thr Cys Glu Pro Asn Ser Glu Ala Cys
1325                1330                1335

Pro Pro Thr Ala Ala Pro Asn Ala Thr Ser Leu Val Pro Ala Thr
1340                1345                1350

Ala Leu Ala Pro Met Ser Asp Cys Leu Gly Leu Ile Pro Pro Arg
1355                1360                1365

Lys Phe Asn Glu Ser Trp Asp Phe Gly Asn Cys Gln Ile Ala Thr
1370                1375                1380

Cys Leu Gly Glu Glu Asn Asn Ile Lys Leu Ser Ser Ile Thr Cys
1385                1390                1395

Pro Pro Gln Gln Leu Lys Leu Cys Val Asn Gly Phe Pro Phe Met
1400                1405                1410

Lys His His Asp Glu Thr Gly Cys Cys Glu Val Phe Glu Cys Gln
1415                1420                1425

Cys Ile Cys Ser Gly Trp Gly Asn Glu His Tyr Val Thr Phe Asp
1430                1435                1440
```

```
Gly Thr Tyr Tyr His Phe Lys Glu Asn Cys Thr Tyr Val Leu Val
    1445                1450                1455

Glu Leu Ile Gln Pro Ser Ser Glu Lys Phe Trp Ile His Ile Asp
    1460                1465                1470

Asn Tyr Tyr Cys Gly Ala Ala Asp Gly Ala Ile Cys Ser Met Ser
    1475                1480                1485

Leu Leu Ile Phe His Ser Asn Ser Leu Val Ile Leu Thr Gln Ala
    1490                1495                1500

Lys Glu His Gly Lys Gly Thr Asn Leu Val Leu Phe Asn Asp Lys
    1505                1510                1515

Lys Val Val Pro Asp Ile Ser Lys Asn Gly Ile Arg Ile Thr Ser
    1520                1525                1530

Ser Gly Leu Tyr Ile Ile Val Glu Ile Pro Glu Leu Glu Val Tyr
    1535                1540                1545

Val Ser Tyr Ser Arg Leu Ala Phe Tyr Ile Lys Leu Pro Phe Gly
    1550                1555                1560

Lys Tyr Tyr Asn Asn Thr Met Gly Leu Cys Gly Thr Cys Thr Asn
    1565                1570                1575

Gln Lys Ser Asp Asp Ala Arg Lys Arg Asn Gly Glu Val Thr Asp
    1580                1585                1590

Ser Phe Lys Glu Met Ala Leu Asp Trp Lys Ala Pro Val Ser Thr
    1595                1600                1605

Asn Arg Tyr Cys Asn Pro Gly Ile Ser Glu Pro Val Lys Ile Glu
    1610                1615                1620

Asn Tyr Gln His Cys Glu Pro Ser Glu Leu Cys Lys Ile Ile Trp
    1625                1630                1635

Asn Leu Thr Glu Cys His Arg Val Val Pro Pro Gln Pro Tyr Tyr
    1640                1645                1650

Glu Ala Cys Val Ala Ser Arg Cys Ser Gln Gln His Pro Ser Thr
    1655                1660                1665

Glu Cys Gln Ser Met Gln Thr Tyr Ala Ala Leu Cys Gly Leu His
    1670                1675                1680

Gly Ile Cys Val Asp Trp Arg Gly Gln Thr Asn Gly Gln Cys Glu
    1685                1690                1695

Ala Thr Cys Ala Arg Asp Gln Val Tyr Lys Pro Cys Gly Glu Ala
    1700                1705                1710

Lys Arg Asn Thr Cys Phe Ser Arg Glu Val Ile Val Asp Thr Leu
    1715                1720                1725

Leu Ser Arg Asn Asn Thr Pro Val Phe Val Glu Gly Cys Tyr Cys
    1730                1735                1740

Pro Asp Gly Asn Ile Leu Leu Asn Glu His Asp Gly Ile Cys Val
    1745                1750                1755

Ser Val Cys Gly Cys Thr Ala Gln Asp Gly Ser Val Lys Lys Pro
    1760                1765                1770

Arg Glu Ala Trp Glu His Asp Cys Gln Tyr Cys Thr Cys Asp Glu
    1775                1780                1785

Glu Thr Leu Asn Ile Ser Cys Phe Pro Arg Pro Cys Ala Lys Ser
    1790                1795                1800

Pro Pro Ile Asn Cys Thr Lys Glu Gly Phe Val Arg Lys Ile Lys
    1805                1810                1815

Pro Arg Leu Asp Asp Pro Cys Cys Thr Glu Thr Val Cys Glu Cys
    1820                1825                1830
```

-continued

Asp Ile Lys Thr Cys Ile Ile Asn Lys Thr Ala Cys Asp Leu Gly
1835                1840                1845

Phe Gln Pro Val Val Ala Ile Ser Glu Asp Gly Cys Cys Pro Ile
1850                1855                1860

Phe Ser Cys Ile Pro Lys Gly Val Cys Val Ser Glu Gly Val Glu
1865                1870                1875

Phe Lys Pro Gly Ala Val Val Pro Lys Ser Ser Cys Glu Asp Cys
1880                1885                1890

Val Cys Thr Asp Glu Gln Asp Ala Val Thr Gly Thr Asn Arg Ile
1895                1900                1905

Gln Cys Val Pro Val Lys Cys Gln Thr Thr Cys Gln Gln Gly Phe
1910                1915                1920

Arg Tyr Val Glu Lys Glu Gly Gln Cys Cys Ser Gln Cys Gln Gln
1925                1930                1935

Val Ala Cys Val Ala Asn Phe Pro Phe Gly Ser Val Thr Ile Glu
1940                1945                1950

Val Gly Lys Ser Tyr Lys Ala Pro Tyr Asp Asn Cys Thr Gln Tyr
1955                1960                1965

Thr Cys Thr Glu Ser Gly Gly Gln Phe Ser Leu Thr Ser Thr Val
1970                1975                1980

Lys Val Cys Leu Pro Phe Glu Glu Ser Asn Cys Val Pro Gly Thr
1985                1990                1995

Val Asp Val Thr Ser Asp Gly Cys Cys Lys Thr Cys Ile Asp Leu
2000                2005                2010

Pro His Lys Cys Lys Arg Ser Met Lys Glu Gln Tyr Ile Val His
2015                2020                2025

Lys His Cys Lys Ser Ala Ala Pro Val Pro Val Pro Phe Cys Glu
2030                2035                2040

Gly Thr Cys Ser Thr Tyr Ser Val Tyr Ser Phe Glu Asn Asn Glu
2045                2050                2055

Met Glu His Lys Cys Ile Cys Cys His Glu Lys Lys Ser His Val
2060                2065                2070

Glu Lys Val Glu Leu Val Cys Ser Glu His Lys Thr Leu Lys Phe
2075                2080                2085

Ser Tyr Val His Val Asp Glu Cys Gly Cys Val Glu Thr Lys Cys
2090                2095                2100

Pro Met Arg Arg Thr
2105

<210> SEQ ID NO 10
<211> LENGTH: 237
<212> TYPE: PRT
<213> ORGANISM: unknown
<220> FEATURE:
<223> OTHER INFORMATION: VIT1_CHICK

<400> SEQUENCE: 10

Ser Ser Ser Ser Ser Ser His Arg His Gly Glu Lys Ala Ala His Ser
1               5                   10                  15

Ser Arg Arg Ser Pro Thr Ser Arg Ala Ala Ser Ala His His Arg Pro
            20                  25                  30

Gly Ser Ser Leu Thr Arg Glu Arg Asn Phe Leu Gly Asp Val Ile Pro
        35                  40                  45

Pro Gly Ile Thr Ile Val Ala Gln Ala Val Arg Ser Asp Asn Arg Asn
    50                  55                  60

-continued

```
Gln Gly Tyr Gln Ala Thr Ala Tyr Val Arg Ser Asp Ala Ala Lys Val
 65              70              75              80

Asp Val Gln Leu Val Val Gln Leu Ala Glu Thr Asn Trp Lys Ala
             85              90              95

Cys Ala Asp Ala Val Ile Leu Pro Leu Lys Ala Gln Ala Arg Met Arg
            100             105             110

Trp Gly Lys Glu Cys Arg Asp Tyr Arg Ile Ala Ala Leu Ala Thr Thr
        115             120             125

Gly Gln Met Ala Arg Lys Leu Ala Val Gln Leu Lys Val Gln Trp Gly
        130             135             140

Ile Ile Pro Ser Trp Ile Lys Lys Thr Ser Thr Ala Leu Met Arg Tyr
145             150             155             160

Val Pro Gly Val Ala Leu Val Leu Gly Phe Ser Glu Ala His Gln Arg
            165             170             175

Asn Pro Ser Arg Glu Leu Ile Val Arg Ala Val Ala Thr Ser Pro Arg
            180             185             190

Ser Ile Asp Thr Val Ile Lys Val Pro Gly Val Thr Leu Tyr Tyr Gln
        195             200             205

Gly Leu Arg Val Pro Phe Thr Leu Ala Leu Gly Ala Ser Ser Ser Ser
        210             215             220

Tyr Glu Thr Arg Asp Ile Thr Ala Trp Asn Phe Leu Pro
225             230             235
```

US 8,753,698 B2

ANTI-HYPERTENSIVE FUNCTIONAL FOOD PRODUCTS

CROSS-REFERENCE TO RELATED APPLICATIONS

This application is the United States national phase of International Application No. PCT/NL2005/000535 filed Jul. 22, 2005, and claims priority to Provisional Application No. 60/589,902 filed on Jul. 22, 2004, the disclosures of which are hereby incorporated in their entirety by reference.

BACKGROUND OF THE INVENTION

1) Field of the Invention

The present invention relates to bioactive egg protein hydrolysates, methods of making active protein hydrolysates and functional foods and food supplements comprising these in suitable amounts. Functional foods, food supplements and the active protein hydrolysates as functional ingredients as such are particularly suited for lowering blood pressure and may be consumed both prophylactically and therapeutically. In addition, the hydrolysates, and compositions comprising these, may be used to treat or prevent one or more components of metabolic disorders and cardiovascular disease risk factors, such as the metabolic syndrome.

2) Description of Related Art

Worldwide cardiovascular diseases have tremendous effects on overall health status and economic involvement of its inhabitants and on economy in general. Every year, 1.5 million people die from cardiovascular disease (CVD) in the Member States of the European Union (European Heart Network). Furthermore, nearly 1.4 million years of life lost in disability are due to CVD of which more than half (over 0.7 million) are lost due to stroke. There is a strong association between the level of blood pressure and the risk of stroke and coronary heart disease and a high percentage of the EU inhabitants suffers from (mildly) elevated blood pressure, the particular group of elderly being even at higher risks.

Hypertension usually coexists within a cluster of risk factors. Angiotensin-I Converting Enzyme (ACE) inhibitors not only lower blood pressure but also positively influence many other aspects of the atherogenic milieu. Evidence for the benefits of ACE inhibitors in reducing cardiovascular morbidity and mortality in patients with myocardial infarction and congestive heart failure is well established by now. Even a mild reduction of blood pressure can positively influence mortality and morbidity rates. Recent analysis of the nature of CVD risk suggests that diet should be receiving greater attention than it has done in the past, as a fundamental, underlying risk factor (European Heart Network, Position Paper, 1998). In this Position Paper it was concluded that this fact implies that provision of a healthy diet needs to be moved to the centre stage of CVD prevention activities.

ACE generates Angiotensin-II having vasopressor activity, including vasoconstriction, by cleaving C-terminal His-Leu off the otherwise inactive Angiotensin-I. It is known that hypertension can be treated by inhibiting the function of ACE. A number of chemical drugs with in vivo ACE inhibitory activity exist, such as Moexipril, Quinapril, Enalapril, Lisinopril, Perindopril, Ramipril, Trandolapril, and Benazepril. Such drugs often have side effects and there is a danger of taking overdoses. In addition they are generally not suitable for prophylactic consumption. There is, therefore, a need for alternative, natural ACE inhibitors, which are not harmful when ingested (prophylactically) by subjects not suffering from raised blood pressure, but which actively lower blood pressure in subjects with (mildly) raised blood pressure. Preferably, such products are ingested either as food supplements (e.g. in the form of tablets, sachets, etc.) or as functional food (e.g. in the form of drinks, semi-solid or solid food products). Regular consumption of such food supplements or functional food products is expected to result in a decrease of costs in the health care sector representing 2% of the cost involved in CVD and a decrease of people suffering from CVD in the EU by 5%. Also, the average disease-free years can likely be extended by at least 3 years. In addition production processes of these products is more environmentally friendly and production costs are much lower compared to chemical drugs.

A number of antihypertensive compositions derived from natural sources have already been described. EP 1 228 708 describes the use of a milk-derived protein and peptide fraction with high blood pressure reducing activity. EP0583074 describes the also milk-derived Val-Pro-Pro comprising peptides with ACE inhibitory activity and fermented food products therewith. WO01/32905 describes the fermentation of casein-containing starting material with lactic acid bacteria for the preparation of antihypertensive peptides. U.S. Pat. No. 6,514,941 relates to casein hydrolysate enriched in hypertensive peptides. WO01/85984 describes the use of whey protein hydrolysates with ACE inhibitory activity and antihypertension activity. EP1094071 relates to a peptide obtained from fish meat for use as an antihypertensive agent.

SUMMARY OF THE INVENTION

It is an object of the invention to provide novel compositions and functional ingredients with ACE inhibiting activity and with antihypertensive activity in vivo.

DESCRIPTION OF THE PREFERRED EMBODIMENTS

General Definitions

The term "food" refers herein to liquid, semi-liquid or solid food products suitable for human and/or animal consumption. Thus beverages are included.

"Functional food" refers to a food product which comprises one or more active ingredients, especially one or more egg protein hydrolysates according to the invention, whereby the active ingredient prevents the development of high or raised blood pressure and/or actively lowers blood pressure in vivo when consumed by subjects with (mildly) raised blood pressure.

"Food supplement" refers to supplements suitable for human and/or animal consumption which comprise a suitable amount of one or more bioactive protein hydrolysates according to the invention as functional ingredient. Supplements may be in the form of pills, sachets, powders and the like.

"Subjects" means any member of the class mammalia, including without limitation humans, non-human primates, farm animals, domestic animals and laboratory animals.

"Food-grade" refers to components which are considered as not harmful, when ingested by a human or animal subject. Food grade components should preferably have a GRAS status.

The term "comprising" is to be interpreted as specifying the presence of the stated parts, steps or components, but does not exclude the presence of one or more additional parts, steps or components. A peptide sequence comprising region X, may thus comprise additional regions, i.e. region X may be embedded in a larger peptide region.

"Effective dose" or "effective amount" refers to a dose sufficient to result in the therapeutic or prophylactic effect in vivo. A therapeutically effective dose is a dose sufficient to reduce blood pressure in vivo (following oral ingestion) of at least about 0.5 mmHg, 1 mmHg, 5 mmHg, 8 mmHg, 10 mmHg, 12 mmHg, 15 mmHg, 20, 30, 50 or 100 mmHg or more. Essentially, any measurable reduction in blood pressure is significant and favourably affects the outcome of cardiovascular morbidity and mortality (see McMahon et al. Lancet 1990, 335: 765-774 and Murray and Lopez 1997, Lancet 349:1498-1504). Both systolic and/or diastolic blood pressure may be reduced in this way.

"ACE inhibitor" or "ACE inhibitory activity" refers herein to the ability of a protein hydrolysate to significantly inhibit ACE-I (Angiotensin-I Converting Enzyme) activity in vitro and/or in vivo. Protein hydrolysates with IC50 values of 0.5 mg/ml or less are regarded as significant in vitro and as (potentially) having significant in vivo ACE inhibitory activity (see Sekiya et al. 1994, Science 45: 513-517). IC50 refers to the concentration at which 50% of enzyme activity is inhibited.

"Eggs" refer herein preferably to chicken eggs, although eggs from other birds may also be used.

"Egg protein hydrolysates" is used herein as a general term to refer to protein hydrolysates (prepared in vitro) of whole eggs, egg fractions (e.g. egg white or egg yolk) or of substantially pure egg proteins, especially lipovitellin, ovomucin, lysozyme, ovalbumin and ovotransferrin.

"Non-hydrolyzed egg protein" or "undigested egg protein" is used herein as a general term to refer to whole eggs, egg fractions (e.g. egg white or egg yolk), or substantially pure egg proteins, especially lipovitellin, ovomucin, lysozyme, ovalbumin and ovotransferrin, which have not been hydrolysed in vitro.

"Metabolic Syndrom" refers to multiple interrelated clinical disorders, including obesity, insulin resistance and hyperinsulinemia, glucose intolerance, hypertension and dyslipidemia (hypertriglyceridemia and low HDL cholesterol levels) as described e.g. in Moller and Kaufman (Annual Rev. of Medicine Vol 56, 45-62).

"Biomarkers" refer to indicators of blood pressure related diseases or syndromes (or individual components of syndromes). For example, blood levels of human CRP (C-reactive protein), a stress-related protein, is a biomarker for CVD risk factors. A reduction in CRP is indicative of a reduced incidence of cardiovascular diseases such as stroke and myocardial infarction; an elevated CRP level is indicative of inflammation of the vascular system, which affects blood pressure and the risk of CVD; other biomarkers are the amount of insulin released following glucose loading (indicative of insulin resistance) and the amount of proteins secreted in the urine.

"Total cholersterol" refers to both LDL- and HDL-cholesterol.

"In vitro digestion simulation" refers herein to the incubation of egg protein hydrolysates or non-hydrolyzed egg protein with enzymes found in the gastrointestinal tract of subject, such as pepsin, chymotrypsin and trypsin and in an order and time frame simulating the physiological in vivo digestion process.

An "active fragment" of a peptide or protein refers to a protein part which is shorter than the full-length protein or protein variant (e.g. obtained by enzymatic hydrolysis or in vivo synthesis) and which shows ACE inhibitory activity.

The term "substantially identical", "substantial identity" or "essentially similar" or "essential similarity" means that two peptide or two nucleotide sequences, when optimally aligned, such as by the programs GAP or BESTFIT using default parameters, share at least a certain percentage of sequence identity as defined elsewhere herein. GAP uses the Needleman and Wunsch global alignment algorithm to align two sequences over their entire length, maximizing the number of matches and minimizes the number of gaps. Generally, the GAP default parameters are used, with a gap creation penalty=50 (nucleotides)/8 (proteins) and gap extension penalty=3 (nucleotides)/2 (proteins). For nucleotides the default scoring matrix used is nwsgapdna and for proteins the default scoring matrix is Blosum62 (Henikoff & Henikoff, 1992, PNAS 89, 915-919).

Sequence alignments and scores for percentage sequence identity may be determined using computer programs, such as the GCG Wisconsin Package, Version 10.3, available from Accelrys Inc., 9685 Scranton Road, San Diego, Calif. 92121-3752 USA or the open-source software Emboss for Windows (current version 2.7.1-07). Alternatively percent similarity or identity may be determined by searching against databases such as FASTA, BLAST, etc.

In addition, reference to an element by the indefinite article "a" or "an" does not exclude the possibility that more than one of the element is present, unless the context clearly requires that there be one and only one of the elements. The indefinite article "a" or "an" thus usually means "at least one".

Further, when reference is made to a nucleotide or amino acid "sequence", it is understood that the physical molecule, i.e. the nucleic acid molecule or protein molecule having that sequence of nucleic acids or amino acids is referred to.

It was surprisingly found that egg protein hydrolysates, especially egg white protein hydrolysates, had significant ACE inhibitory activity in in vitro assays and showed significant anti-hypertensive activity in rats in vivo.

Initially in silico analysis (using proprietary in house software that quantitatively scores and ranks proteins) was used to identify target proteins in chicken eggs, which comprise peptides with ACE inhibitory activity and, hence, have a high potential of being antihypertensive in vivo. A selection criterion was that the calculated score exceeded that of the reference protein β-casein, containing known ACE inhibitory peptides. Based on the overall quantitative score and ranking, five target proteins were identified, which comprise ACE inhibitor peptides and may exert in vivo antihypertensive activity when enzymatically hydrolyzed and optionally enriched for active peptides following enzymatic hydrolysis:lipovitellin (see e.g. SEQ ID NO: 1, 2, 7 and 8), a protein found in egg yolk, ovomucin (see e.g. SEQ ID NO: 6 and 9), lysozyme (see e.g. SEQ ID NO: 4), ovalbumin (see e.g. SEQ ID NO: 8) and ovotransferrin (see e.g. SEQ ID NO: 5) (all four found in egg white).

In order to analyze whether and how egg white and/or egg yolk proteins could be used to manufacture hydrolysates with significant ACE inhibitory activity a number of experiments were carried out as further described in the Examples.

It is one embodiment of the invention to provide a method for making egg protein hydrolysates with ACE inhibitory activity and with anti-hypertensive activity. The method comprises the steps of:

1. providing a liquid solution, preferably an aqueous solution, which comprises one or more target proteins,
2. Optionally heating the solution to about 90° C. for about 5-20 minutes, preferably 15 minutes, to denature the proteins and/or inactivate (possibly present) protease inhibitors,
3. adjusting the pH to a pH at which the hydrolytic enzyme(s) to be used is (are) active, preferably the optimal pH value for the hydrolytic enzyme(s) to be used, 4. when the composition has reached the hydrolysis temperature suitable for the hydrolytic enzyme(s) to be used, preferably the optimal temperature with respect to hydrolyzing activity, adding a suitable amount of hydrolytic enzyme(s), preferably about 2% hydrolytic enzyme(s) with respect to the total target protein fraction (w/w),
5. incubating the solution for at least about 3 hours, while stirring
6. optionally adding an additional amount of enzyme(s) (2% w/w) and further incubating the solution for about 2 to 3 hours while stirring
7. optionally inactivating the enzyme(s) by e.g. heat treatment, e.g. 15 minutes at 90° C.

Provided is also a hydrolysate obtainable by the above method and a composition, preferably a food or food supplement composition, comprising a suitable amount of such a hydrolysate.

The solution may be concentrated or freeze dried, e.g. lyophilized, and stored at room temperature for further use, such as in vitro ACE inhibition assays, for peptide enrichment (see below) or further purification of peptides or for the production of food supplements or food products comprising effective amounts of hydrolysate.

It was found that in some instances removal of the solid component by centrifugation led to an increase in ACE inhibitory activity of the soluble fraction by a factor of 1.5 to 2, compared to the activity of the whole hydrolysate. Optionally, the soluble fraction may thus be isolated and used. The solid fraction may be removed by e.g. centrifugation for about 15 minutes at 4,500 g, or equivalent conditions. Solid fractions may also be removed by filtration or by other separation techniques. For other target proteins, removal of the solid fraction resulted in a reduction of ACE inhibitory activity of the soluble fraction, which is undesirable. For these target proteins the solid fraction is preferably retained or re-added to the product or used as (part of) the active food or food supplement ingredient.

It is understood that some steps in the hydrolysis method may be modified without altering the properties of the resulting hydrolysate. For example, the incubation steps 5 and 6 may be replaced by a single enzyme incubation step of about e.g. 4-5 or 5-6 hours. A skilled person will easily be able to adapt the above hydrolysis protocol for optimal use. It is preferred that hydrolysis is carried out in water instead of buffer solutions, especially for large scale production for human and/or animal consumption, as high amounts of salts are undesirable. In general, for hydrolysis optimization of the amount of enzyme used, pH, temperature and incubation times may be required. An example of suitable hydrolysis protocols are provided in the Examples.

The protein component of the liquid solution according to step 1 may be selected from one or more of the following: (fresh) whole egg, isolated egg white, isolated egg yolk, egg powder, egg white powder, egg yolk powder, substantially pure whole protein compositions of ovalbumin, lysozyme, ovotransferrin, ovomucin and/or lipovitellin. Examples of suitable target protein sources are commercially available protein compositions or egg fraction compositions, such as egg white powder. Lysozyme may for example be obtained from Belovo (100% pure protein), ovotransferrin may be obtained from Sigma-Aldrich (81.3% pure protein) or from Belovo (89.5% protein), ovomucin may be obtained from Belovo, ovalbumin may be obtained from Worthington (75.7% protein) or from Interchema (70.8% protein), Egg yolk may be obtained from NIVE (31.6% protein) and Egg white may be obtained from NIVE (79.7% protein). Obviously, alternative commercial sources may be used or known purification methods may be used to purify one or more target proteins from eggs or egg fractions. Proteins such as lipovitellin, lysozyme, ovotransferrin, ovomucin and ovalbumin may also be produced using recombinant DNA technology as known in the art. For example, protein fragments or full length proteins of any of SEQ ID NO: 1-10 (or variants thereof) may be synthesized de novo using chemical synthesis or cloned and expressed in recombinant host cells. Thus it is envisaged that as a starting material whole egg, egg yolk, or egg white may be used that is enriched in one or more of lipovitellin, lysozyme, ovotransferrin, ovomucin and ovalbumin (or variants of any of these or fragments thereof), via for example appropriate diet of the egg producing animal(s) or even via transgenic animal(s).

"Variants" of the target proteins of SEQ ID NO: 1-10 include proteins which are essentially similar to those of SEQ ID NO: 1-10, such as proteins having an amino acid sequence which comprises at least 60%, 70%, 80%, 90%, 95%, 98%, 99% or 100% sequence identity to any of SEQ ID NO: 1-10. Such variants may be synthesized de novo, isolated or cloned from natural sources or identified in silico.

In one embodiment of the invention the eggs used as protein source are not fresh, but may have been stored for longer periods at e.g. room temperature, at 4° C. or in powder form. It was found that the ACE inhibitory activity is not negatively affected by the egg source not being fresh. This has advantages in the hydrolysate production process as for example cooling of the eggs is not required prior to use. Storage of eggs or egg fractions at room temperature or at temperatures between about 4° C. and room temperature is possible for at least 6 weeks without loss of activity.

Alternatively, the target proteins may be extracted from eggs and subsequently purified. For example the egg white fraction may be separated using known methods and a specific target protein may be purified by cation and anion exchange chromatography, gel permeation chromatography, affinity chromatography and other methods known in the art. Ovotransferrin can for example be purified by metal chelating chromatography, while heparin affinity chromatography may be used for the isolation of glycoproteins. The concentration of lysozyme in egg white is high (3-4%) as compared to other sources of lysozyme. A process used routinely for lysozyme purification is Cation Exchange Chromatography. Lysozyme is bound to a cation exchanger at the pH as is (pH 9). This may be done in a stirred tank reactor or in a chromatography column. After elution from the adsorption particles by salt, lysozyme is pure enough for food applications. Anion Exchange Chromatography at pH 4 is required for further purification in order to obtain highly pure lysozyme, suitable for pharmaceutical applications. The advantages of this purification process are that the starting material (egg white) is not altered, the process is easily upscalable, for food applications just one adsorption process is needed and the biological activity is retained. Thus, in one embodiment lysozyme is purified using Cation Exchange Chromatography.

Further purification of any one of the target proteins, steps such as membrane ultrafiltration and diafiltration may be applied.

The enzyme suitable for hydrolysis may in principle be any food grade protease or protease mixture from a variety of sources, such as plants, animals, or microorganisms such as fungi or bacteria. For example, Newlase F comprises an acid protease derived from *Rhizopus niveus*, Promod 184P comprises a protease from *Ananas comosus*, Promod 258P comprises proteinase from *Carica papaya* (papain) and proteinases and peptidases from *Aspergillus* spp., Pepsin 389P comprises an animal acid protease from porcine gastric mucosa, Alcalase comprises a *Bacillus licheniformi* protease mix with as the main enzyme an endoproteinase.

It was found that specific target protein-protease combinations release bioactive peptides, resulting in hydrolysates with ACE inhibitory activity. Preferred enzymes to be used for the preparation of protein hydrolysates are provided in Table 1, together with the optimal conditions for their use.

TABLE 1 enzymes for use in hydrolysate production

| Enzyme | pH range | Temperature range (° C.) | Supplier | Optimal pH and Temperature |
|---|---|---|---|---|
| Newlase F | 2-7 | 30-55 | Amano Enz. | pH 3; 50° C. |
| Pepsin 389P | 2-5.5 | 40-55 | Biocatalysts | pH 3; 50° C. |
| Promod 258P | 3.5-7.5 | 40-50 | Biocatalysts | pH 5.5; 45° C. |
| Promod 184P | 5-7 | 45-55 | Biocatalysts | pH 6; 50° C. |
| Flavourzyme | 5-7 | 30-60 | Novozyme | pH 7; 50° C. |
| Alcalase | 6.5-8.5 | 40-65 | Novozyme | pH 8; 60° C. |
| PEM | 6-8 | 30-45 | Novozyme | pH 8; 50° C. |
| PTN 6.0S | 6-8 | 30-45 | Novozyme | pH 7; 45° C. |
| Corolase PP | 6-10 | 30-55 | AB Enzymes | pH 8.5; 45° C. |
| Protex 6L | 7-10 | 25-70 | Genencor | pH 9.5; 60° C. |

Out of the enzymes tested the following food grade proteases (or protease mixtures) were found to be especially suitable: Newlase F, Promod 258P, Alcalase, PEM (Proteolytic Enzyme Mix), PTN (Pancreatic Trypsin Novo) and Protex 6L. It is understood that other endo- and/or exo-proteases (or mixtures) may be used. A skilled person can determine the suitability by making a hydrolysate as described and testing the ACE inhibitory activity using an in vitro assay as described elsewhere herein.

Without limiting the scope of the invention it is thought that enzymes which release a relative high proportion of single amino acids due to exo-protease activity are less suitable, while enzymes which release a relative high proportion of di- and/or tri-peptides (due to endo- and exo-protease activity or only endo-protease activity) are most suitable. Suitably the enzyme(s) release(s) less than about 10% free amino acids, preferably less than about 8%, 7%, 6% or 5%. Preferably, the enzymes used release relative high proportions of di- and/or tri-peptides, e.g. at least more than 10%, 15%, 20%, 30%, 40%, 50% or more.

The protein hydrolysates according to the invention thus preferably comprise a high proportion of di- and/or tri peptides of the target protein(s), preferably at least 10, 20, 30, 40, 50, 60, 70, 80% or more. In one embodiment peptides of longer chain length and higher molecular weight, such as peptides with 4, 5, 6, 7, 8 or more amino acids, are therefore preferably present in relatively low amounts (preferably less than 10% of the total target protein fraction) or absent.

In one embodiment a hydrolysate according to the invention can thus be characterized by the percentage of target-protein derived di- and/or tri-peptides (and the distribution of peptide chain length in the protein fraction) and/or by the molecular weight distribution of the target peptides. For example, a hydrolysate may comprise at least 30, 40, 50, 60, 70, 80, 90, 95, 99 or 100% target peptides of less than 0.5 kD. Example 13 illustrates the relationship between molecular weight distribution of target protein hydrolysates, degree of hydrolysis and activity of the hydrolysates. Preferred molecular weight distributions are, therefore, illustrated in Example 13, and comprise for example about 70:10:20, 45:21:34, 70:16:14, 98:1:1, 99:1:0, 85:10:5, 90:1:9, 92:4:4 and 53:17:30 (expressed as percentage of fragments having a molecular weight of <0.5 kD: between 0.5 and 1.0 kD:>1 kD). Fragments of less than 0.5 kD correspond to fragments of less than 4-5 amino acids, while fragments of about 0.5-1.0 kD correspond to 4-9 amino acids and fragments of above 1 kD correspond to peptide fragments of above 9 amino acids. Thus, any of the target proteins, such as proteins comprising the amino acid sequence of SEQ ID NOs 1-10, or variants thereof, may be hydrolyzed to generate peptides comprising these stretches of contiguous amino acids. Preferably, the degree of hydrolysis of a target protein is at least about 15%, 20%, more preferably at least 30% or more. Thus, in one embodiment compositions comprising a plurality of fragments selected from one or more of 2 contiguous amino acids, 3, 4, 5, 6, 7, 8, 9 contiguous amino acids of any of SEQ ID NO: 1-10, or of variants thereof, are included.

A molecular weight distribution of a hydrolysate may thus comprise for example 40-70% target peptides of less than 0.5 kD and 30-50% peptides between 0.5 and 1 kD, or the like. The molecular weight distribution, peptide chain length distribution and maximum peptide weight of the hydrolysate can be determined by methods known in the art, such as SDS-PAGE analysis, HPLC analysis, MALDI-TOF (Matrix-Assisted Laser Desorption/Ionisation Time-of-Flight mass spectrometry, as described by Kaufmann, J. Biotechn 1995, 41:155-175 and Soeryapranata et al. 2002, J. Food Sci. 67:534-538), HP-GPC (high performance gel permeation chromatography, as described in Terheggen-Lagro et al. BMC Pediatrics 2002, 2:10) and Edman degradation (Siemensma et al. Trends Food Sci Technology 1993, 4:16-21), see also Example 13. The maximum molecular peptide weight of the target protein is preferably less than 10 kD, more preferably less than 5 kD, more preferably less than 4 kD, 3 kD, 2 kD, 1 kD, 0.5 kD or less than about 0.3 kD.

In a specific embodiment the proportion of short peptides, such as di- and tri-peptides is enriched, whereby the ACE inhibitory activity of the resulting hydrolysate is increased by a factor of at least 1.5, a factor of 2, preferably a factor of 3 or more. The enrichment of bioactive peptides can be achieved by filtration of the hydrolysate comprising the target protein derived peptides through one or more membrane filters (e.g. ultrafiltration or nanofiltration filters), preferably membrane filters with a molecular weight cut-off of 0.3 kD, 0.5 kD, 1 kD, 2 kD, 3 kD, 4 kD, 5 kD to 10 kD, more preferably from 2 kD to 5 kD are used. Target protein hydrolysates enriched for short, low molecular weight peptides of about 2, 3, 4 and/or 5 amino acids in length and having enhanced ACE inhibitory activity are therefore provided herein. Preferably enrichment with a size cut off of 2-3 kD is used. For example the ACE inhibitory activity of a hydrolysate comprising ovotransferrin peptides and of a hydrolysate comprising lysozyme peptides was shown to be increased following enrichment of short peptides (see Examples). Such enriched hydrolysates preferably comprise an improved antihypertensive activity in vivo. In addition, smaller amounts may be effective on a daily basis, which enables the preparation of food supplements or food products of smaller volume.

Membrane filtration may also be used to remove undesired impurities which may be present in the hydrolysates and which may influence activity of the peptides.

It is also envisaged to produce bioactive protein hydrolysates by using combinations (mixtures) of target proteins and/or enzymes, optionally followed by enrichment of low molecular weight peptides, such as for example di- and/or tri-peptides.

Alternatively a composition resembling a protein hydrolysate product of this invention can be made de novo making use of chemical synthesis methods. In particular a di- and a tri-peptide library can be made by combinatorial chemistry thereby forming all possible combinations of dipeptides and tripeptides. From this pool, or library of di- and tripeptides a mixture can be composed having essentially the same activity on blood pressure as the hydrolysates described above.

The following target protein-enzyme combinations resulted in hydrolysates with ACE inhibitory values of about 50%, 55%, 60%, 65%, 70%, 80% or more at 0.5 mg/ml hydrolysate (for details see Examples):
Target Protein—Enzyme
Lysozyme—Alcalase
Lysozyme—Protex 6L
Lysozyme—PEM
Lysozyme—PTN
Ovomucin—PEM
Ovomucin—Alcalase
Ovomucin—Protex 6L
Ovomucin—PTN
Ovotransferrin—Newlase F
Ovotransferrin—Promod 258P
Ovotransferrin—PTN
Ovotransferrin—PEM
Ovotransferrin—Protex 6L
Ovalbumin—Promod 258P
Egg yolk—Alcalase
Egg yolk—Protex L6
Egg yolk—PEM
Egg yolk—Newlase F
Egg white—Alcalase
Egg white—Promod 258P A list of the ten most active hydrolysates resulted in a ranking according to ACE inhibitory activity (in vitro assay) as follows (from most active to less active):
1. Ovotransferrin—Newlase F; Ovotransferrin—PTN
2. Ovomucin—Alcalase; Ovotransferrin—PEM; Lysozyme—PEM
3. Egg yolk—Protex L6; Ovalbumin—Promod 258P; Ovotransferrin—Promod 258P; Lysozyme—Alcalase; Lysozyme—Protex 6L.

For commercial purposes, adaptation to large scale production, e.g. 500, 1000, 1000 liter or more, of raw starting material and/or protein hydrolysate production methods is a matter of routine experimentation to a person skilled in the art desired.

Provided are thus egg protein hydrolysates, generated as described above and optionally further enriched and/or purified, with significant ACE inhibitory activity and with significant anti-hypertensive activity in vivo. Also provided are compositions, especially food and/or food supplement compositions comprising a suitable amount of an hydrolysate according to the invention, see below.

In another embodiment non-hydrolysed egg protein or partially hydrolyzed egg protein is provided and uses thereof, as well as food supplements and food products comprising an effective amount of at least one non-hydrolyzed egg protein, especially at least one non-hydrolyzed egg protein selected from whole egg, whole egg yolk, whole egg white, ovotransferrin, ovomucin, lysozyme and/or ovalbumin. It was surprisingly found (using digestion simulation) that hydrolysis by proteases present in the gastrointestinal tract of human and/or animal subjects is effective in releasing bioactive peptides from the target protein(s). An in vitro hydrolysis is, therefore, not per se an essential step, although it may be preferred in order to minimize variation of the in vivo effect, which may result from variation between subjects (one subject may have higher digestive enzyme amounts and/or activities than another) and/or from variation in food composition and texture (leading to variation in retention time in the different gastrointestinal compartments).

When hydrolyzed egg protein(s) are used for the preparation of a food supplement or food product, it is preferred that the activity of the hydrolysate is not modified in vivo, or is at least not substantially modified or modified in a negative way (reducing activity). Whether a hydrolysate is "fully hydrolyzed", in the sense that subsequent contact with gastrointestinal enzymes has no effect on the hydrolysate's biological activity, can be tested by carrying out an in vitro digestion simulation assay. In this assay the hydrolysate is incubated with pepsin, trypsin and chymotrypsin and the ACE inhibitory activity of the starting hydrolysate is compared with the ACE inhibitory activity of the pepsin/trypsin/chymotrypsin treated hydrolysate (see Examples for further detailes). Preferably digestion simulation (and in vivo digestion) does not alter the ACE inhibiting activity of the hydrolysate or the food supplement or food product comprising the hydrolysate.

Further provided are food supplements and food products comprising at least one hydrolysate according to the invention in an effective amount and/or at least one non-hydrolyzed egg protein (or partially hydrolyzed egg protein) in an effective amount. Significant ACE inhibitory activity is defined as 0.5 mg/ml protein hydrolysate (or less) being able to inhibit about 50% (or more) of ACE activity, for example using an in vitro assay. In vitro assays for determining ACE inhibitory activity are known (see e.g. Matsui et al. 1992, Biosc. Biotech. Biochem 56, 517-518) and described in the Examples. Suitably a known ACE inhibitor is used as reference, e.g. captopril. A significant anti-hypertensive activity is herein defined as the ability of the hydrolysate to lower blood pressure in vivo, as may be determined for example in test animals, such as SHR (Spontaneous Hypertensive Rats), wherein (diastolic and/or) systolic blood pressure (SPB) is measured at regular intervals following oral ingestion or in human trials. Control rats may be normotensive rats such as Wistar rats or WKY. Methods for measuring blood pressure in model animals are known in the art, such as telemetry and tail cuff methods (see Van Vliet et al. 2000, J Pharmacol Toxicol Methods. 44(2):361-73). Telemetric devices and Tail cuff blood pressure analyzers are commercially available.

Food supplements and food products comprising at least one protein hydrolysate according to the invention and/or at least one non-hydrolyzed egg protein according to the invention may be made as known in the art. Food supplements may for example be in the form of any dosage form such as tablets, pills, powder sachets, gels, capsules, and the like. Intake by the subject is preferably oral. Food products may be in the form of drinks (e.g. 100 ml bottles, 150 ml solutions), solid or semi-solid foods, such as snacks, deserts, sauces, whole meals, etc. Preferably the food product is a product which is consumed on a regular basis, preferably daily, such as staple foods (e.g. bread, noodles, soft drinks, dairy products such as cheese, yoghurt, fermented dairy products, milk, butter etc.). The bioactive component may thus be added to a food base or may be incorporated into the food product during its production process. Thus, any existing food or food supplement products comprising a hydrolysate according to the invention are included herein.

In a preferred embodiment the food product is a drink, preferably based on a fruit juice or vegetable juice, although milk based drinks are also included. The drink may be made in daily dosage volumes of 50 ml, 100 ml, 150 ml, 200 ml or more. It is understood that the food supplement or food product may further comprise additional food-grade ingredients, such as but not limited to flavorings, vitamins, minerals, stabilizers, emulsifiers, other biologically active ingredients, food bases/nutrients such as a protein, carbohydrate and/or fat component, and the like. The egg protein hydrolysate or non-hydrolyzed egg protein may be added at any stage during the normal production process of the food product/food supplement.

The food product/supplement may also comprise other inactive ingredients and carriers, such as e.g. glucose, lactose, sucrose, mannitol, starch, cellulose or cellulose derivatives, e.g. carboxymethylcellulose (CMC), magnesium stearate, stearic acid, sodium saccharin, talcum, magnesium carbonate and the like. It may also comprise water, electrolytes, essential and non-essential amino acids, trace elements, minerals, fiber, sweeteners, flavorings, colorants, emulsifiers and stabilizers (such as soy lecithin, citric acid, esters of mono- or di-glycerides), preservatives, binders, fragrances, and the like.

The effective dose which needs to be added depends on a number of factors, such as the subject (e.g. human or animal), the dosage form (daily, several times a day, weekly) and product composition and/or texture. The daily effective dose of protein hydrolysate or non-hydrolyzed protein will range between about 50 mg/kg body weight to 100 mg/kg, 500 mg/kg to 1000 mg/kg body weight, or more. However, for highly active hydrolysates amounts of about 10 mg/kg/day or less may be sufficient. It is within the realm of a skilled person to determine the effective dose using routine experimentation. In one embodiment a food or food supplement composition comprising a dose of 10 g, 20 g, 30 g, 40 g or more hydrolysate is provided. Such composition is suitable for daily intake.

For food supplements in the form of pills or capsules, a coating may be added which changes the place and/or time of release in vivo of the bioactive peptides. Slow release formulations are known in the art.

The functional food products and food supplements according to the invention preferably lower blood pressure after regular, preferably daily, intake of an effective dose. The effect on blood pressure will be seen after a few weeks, such as 3, 4, 5, 6 or 7 weeks, depending on the dosage form and intake.

Such functional food products or food supplements may be labeled as having a blood pressure lowering effect and may be ingested as a treatment, by subjects having been diagnosed a slightly raised or high blood pressure. A normal blood pressure reading for a human adult is about 120 mmHg (systolic)/80 mmHg (diastolic). Raised or high blood pressure can be divided into different levels, such as Borderline (120–160/90–94), Mild (140–160/95–104), Moderate 140–180/105–114) and Severe (160+/115+). The food products and supplements according to the invention are especially suited for treatment of the borderline, mild and moderate group. They may be taken alone or in combination with chemical drugs (for which then the dosage may be reduced) or other blood pressure lowering products.

Alternatively, the product may be ingested prophylactically by subjects at risk of developing raised/high blood pressure or by any healthy subject. In humans suffering from raised blood pressure essentially any reduction in blood pressure (mmHg) following oral intake of compositions according to the invention favorably affects morbidity and mortality. A reduction of diastolic blood pressure by only 1 mmHg (or less), 5 mmHg, 8 mmHg, 10 mmHg, 12 mmHg, 15 mmHg, 20 mmHg, 30 mmHg, 40 mmHg or more following oral ingestion of food supplements or compositions according to the invention is encompassed herein. Further encompassed is (additionally or alternatively) a reduction of systolic blood pressure by the same amounts as herein above.

In another embodiment, the hydrolysate(s) according to the invention or compositions comprising a suitable amount of one or more hydrolysates, are used for the treatment or prophylaxis of metabolic syndrome (or one or more individual components of metabolic syndrome), for the reduction of total cholesterol and/or LDL-cholesterol, for the reduction of blood CRP levels, for treatment or prophylaxis of insulin resistance (i.e. diabetes; diabetes type 2 or non-insulin dependent diabetes mellitus ot glucose intolerance), and/or for the reduction of total urinary protein levels. Thus, biomarkers can be measured following regular intake of compositions comprising one or more hydrolysates according to the invention, and the effect of the hydrolysate on the biomarker can be determined. Hydrolysates may therefore be used to modulate one or more biomarkers, and thereby have a beneficial health effect. A method for modulating biomarkers using hydrolysates according to the invention is herein included.

Preferably, total blood cholesterol levels and/or LDL cholesterol levels are reduced by at least 10 mg/L, 15 mg/L, 20 mg/L, 25 mg/L, 30 mg/L or more following regular intake of hydrolysate(s) (e.g. after one, two, or three weeks intake of a suitable amount). Routine experimentation can be used to determine a suitable amount.

Blood CRP levels are preferably reduced by 0.3 mg/L, 0.5 mg/L, 1.0 mg/L or more. Urinary protein levels are preferably reduced by 2%, 5%, 10% or more.

It is understood that any combinations of the above are included herein. Thus, intake of hydrolysates according to the invention may be suitable for reducing both systolic and diastolic blood pressure, total and LDL cholesterol, CPR levels etc.

It is understood that hydrolysates comprising anti-hypertensive peptides according to the invention may also be generated by other methods, such as fermentation by bacteria or other microorganisms (yeast, other fungi), chemical synthesis or expression in transgenic host cells or host organisms. For example, a DNA sequence encoding a active peptide may be operably linked to a suitable promoter (preferably a strong promoter) and expressed in plant cells, tissues or organs and/or transgenic plants. Also, a DNA sequence may be designed which comprises sequence stretches encoding several active peptides which may be expressed under a single promoter. The peptides may be separated by spacer sequences, such as sequences encoding amino acids recognized and cleaved by proteases, so that the active peptides can subsequently be released by enzymatic hydrolysis.

SEQ ID NO 1: VIT2_CHICK amino acid sequence
SEQ ID NO 2: VIT2_CHICK amino acid sequence
SEQ ID NO 3: APV1_CHICK amino acid sequence
SEQ ID NO 4: LYC_CHICK amino acid sequence
SEQ ID NO 5: TRFE_CHICK amino acid sequence
SEQ ID NO 6: Q98UI9 amino acid sequence
SEQ ID NO 7: VIT1_CHICK amino acid sequence
SEQ ID NO 8: OVAL_CHICK amino acid sequence
SEQ ID NO 9: Q98UI9 amino acid sequence
SEQ ID NO 10: VIT1_CHICK amino acid sequence The following non-limiting Examples illustrate the products and processes according to the invention.

EXAMPLES

Example 1

In Silico Analysis 1.1 Method

An in-house peptide database was built for all known ACE inhibiting peptides containing sequence data and quantitative activity data (IC50 values). This database was analyzed against a second database comprising all chicken/egg proteins. Signal sequences were removed during analysis, as well as peptides which were not full length mature peptides. The programs used calculated scores, which reflect the probability of peptides being present in the target protein sequence which have ACE inhibitory activity.

1.2 Results

The following results were obtained based on activity predictions and taking peptide length into consideration, with priority on short peptide lengths.

| Source<br>EY = egg yolk<br>EW = egg white | Protein | Weighted score<br>(x 1000 score/AA) |
|---|---|---|
| EY | Vit 2 Lipovitellin II<br>(VIT2_CHICK; SEQ ID NO: 1) | 15.8 |
| EY | Vit 2 Lipovitellin I<br>(VIT2_CHICK; SEQ ID NO: 2) | 9.6 |
| EY | Apovitellenin I precursor<br>(APV1_CHICK; SEQ ID NO: 3) | 9.5 |
| EW | Lysozyme C precursor<br>(LYC_CHICK; SEQ ID NO: 4) | 8.6 |
| EW | Ovotransferrin precursor<br>(TRFE_CHICK; SEQ ID NO: 5) | 8.3 |
| EW | Ovomucin alpha-subunit<br>(from 1741)<br>(Q98UI9; SEQ ID NO: 6) | 6.0 |
| EY | Vit 1 Lipovitellin I<br>(VIT1_CHICK; SEQ ID NO: 7) | 5.6 |
| EW | Ovalbumin<br>(OVAL_CHICK; SEQ ID NO: 8) | 5.3 |
| EW | Ovomucin alpha-subunit<br>(to 1740)<br>(Q98UI9; SEQ ID NO: 9) | 5.0 |
| EY | Vit 1 Lipovitellin II<br>(VIT1_CHICK; SEQ ID NO: 10) | 3.8 |
| Reference<br>protein | Beta casein precursor<br>(CASB_BOVIN) | 4.5 |

Target proteins with the highest weighted scores comprise peptides with ACE inhibitory activity (in number and in total activity) and these proteins are, therefore, promising sources for hydrolysates with ACE-inhibiting properties. The most promising target proteins were lipovitellin I and II, lysozyme, ovotransferrin, ovomucin and ovalbumin.

Example 2

Optimized Protocols According to the Invention 2.1 Protocol for the Hydrolysis of Egg Proteins Protein fraction (3%) is dissolved in water Solution is stirred The solution is incubated for 15 minutes at 90° C. (not for Lysozyme; coaggulation)

After cooling down to the desired temperature the pH is adjusted to the desired pH and enzyme is added (2% enzyme with respect to protein fraction (w/w))

Solution is incubated for 3 hour while stirred.

Additional amount of enzyme is added (again 2% w/w)

Solution is incubated for an additional 2 to 3 hour under stirring

The enzyme is inactivated by incubation at 90° C. for 15 minutes in a waterbath.

The solution is freeze dried and stored at room temperature.

2.2 Protocol for the In Vitro Digestion Simulation of (Hydrolysed) Samples

A 4% protein (hydrolysate) sample solution is made

The pH is set to 2

From a pepsin solution of 10 mg/ml an amount is added to a ratio of 1/250 (w/w)

The solution is incubated for 2 hours at 37° C. in a waterbath under shaking

Subsequently, the pH is set to 6.5

From a solution containing 10 mg/ml trypsin and 10 mg/ml chymotrypsin an amount is added to a ratio of 1/250 (w/w) for both enzymes The solution is incubated for 2.5 hours at 37° C. in a waterbath under shaking The enzymes are inactivated by incubation at 90° C. for 15 minutes Samples are freeze dried and stored at room temperature 2.3 Protocol for Determination of Ace Inhibitory Activity of Hydrolysates in a Microtiter Plate ACE inhibitory activity can be measured in vitro using a spectrophotometry based assay. The assay is based on the liberation of hippuric acid from Hip-His-Leu substrate catalyzed by ACE.

Solutions Used:

0.1 M borate buffer, pH8.3, containing 300 mM NaCl 5 mM EDTA.2Na solution 0.5 M Bicine containing 1 M NaCl 0.25 M NaOH 50 mU/ml ACE 50 mM 2,4,6-trinitrobenzenesulfonic acid (TNBS) in 0.1 M $Na_2HPO_4$ 5 mM Hippuryl-L-Histidyl-L-Leucine (Hip-His-Leu) in borate buffer, containing 1 mg/ml Lactoferrin protein (hydrolysate) solutions (0.500 mg/ml, 0.167 mg/ml, 0.055 mg/ml, 0.019 mg/ml)

Reference solution, 0.5 mg/ml Egg white/Alcalase hydrolysate

Incubation Protocol of the Miniaturized Ace Inhibition Assay:

|  | sample | blank 1 | control | blank 2 |
|---|---|---|---|---|
|  | volumes (μl) | | | |
| hydrolysate | 25 | 25 | — | — |
| water | 25 | — | 50 | 25 |
| Hip-His-Leu |  | 25 |  |  |
| EDTA.2Na | — | 25 | — | 25 |
| ACE |  |  | 25 |  |
|  | 2 h 37° C. | | | |
| EDTA | 25 | — | 25 | — |
| water | — | 25 | — | 25 |
| NaOH |  |  | 15 |  |
| Bicine |  |  | 35 |  |
| TNBS |  |  | 25 |  |
|  | incubation 15 minutes at 37° C. | | | |
|  | measurement of the absorbance at 405 nm | | | |

EDTA denatures ACE (100% ACE inhibition)
Lactoferrin, native protein, is added to all the wells to zero-balance the test
Bicine (buffer) adjusts the pH of all the wells to pH 9.1, i.e., the optimal pH for the TNBS reaction Calculation of Ace Inhibition:

$$\% \text{ inhibition} = \frac{(\text{control-blank 2}) - (\text{sample-blank 1})}{(\text{control-blank 2})} \times 100$$

2.4 Further (Optimized) Hydrolysis of Ovomucin with Alcalase

Protocol for the DH Determination by TNBS Method

Solutions:

0.21 M Sodium phosphate buffer pH8.2

0.21 M $NaH_2PO_4.H_2O$ (25 ml solution)

0.21 M $Na_2HPO_4.2H_2O$ (500 ml solution)

mix solutions to pH 8.2

0.05% TNBS

Dilute TNBS stock (5% solution) to 0.05% in MQ cover reagent tube with aluminium foil and store in dark place 1% SDS solution Leucine standard (stock 3 mM Leucine)

Dissolve Leucine in 1% SDS solution. Dilute the stock solution 20×, 10×, 4× en 2× with 1% SDS for analysis Blank Dilute non-hydrolysed sample in 1% SDS to a protein concentration of 0.5 mg/ml Samples Dilute hydrolysed protein in 1% SDS to a concentration of 0.5 mg/ml in duplo Analysis:

Pipet 15 μl sample (Leucine standard or sample) in microwell. Measure each dilution in twofold in plate (Costar, non-binding plate)

Add 45 μl 0.21 M sodium phosphate buffer pH 8.2

Add 45 μl 0.05% TNBS. Cover plate with aluminium foil. Incubate plate for 60 minutes in a 50° C. stove.

After incubation add 90 μl 0.1 N HCl

Measure absorption at 340 nm (microplate reader)

Calculation of degree of hydrolysis (DH):

Make calibration line of Leucine standard. This calibration line is used to convert absorption values of samples to $NH_2$-equivalents. Correct mmol $NH_2$-equivalents in sample for mmol eq. in non hydrolysed sample.

Example: $NH_2$ due to hydrolysis=0.78 mM Leucine $NH_2$, 0.78 mM*15 (sample volume)*$10^{-6}$=$1.17*10^{-5}$ meq. The protein concentration of the sample was 0.5 mg/ml, so 15 μl contains 7.5 μg protein. h=$1.17*10^{-5}$ meq/$7.5*10^{-6}$=1.56 meq/g. h tot eiwit (value depends on protein)=7800 meq/kg. % DH=(1.56/7.8)*100%=20%

Results

Experiment 1

3% Solution of Ovomucin, pH8, 60° C., Alcalase

| Hydrolysis time total (hours) | Enzyme (%) | DH (%) | ACE inhibition IC50 (mg/ml) |
|---|---|---|---|
| 4 | 2% t = 0 | 0 | >2 |
| 5 | 4% total (after 4 hours plus 2%) | 5.0 | 0.76 |
| 6 | 4% total | 7.7 | 0.66 |
| 7 | 6% total (after 6 hours plus 2%) | 12.9 | 0.45 |
| 7.5 | 6% total | 15.0 | 0.43 |

NB:
During first hours no optimal hydrolysis!

Experiment 2
3% Solution of Ovomucin/Alcalase Hydrolysate, pH8, 60° C., Alcalase

| Hydrolysis time total (hours) | Enzyme (%) | DH | ACE inhibition IC50 (mg/ml) |
|---|---|---|---|
| 5 | 4% total (2% t = 0, after 3 hours plus 2%) | 12.0 | 0.54 |
| 8 | 6% total (t = 5 plus 2%) | 21.7 | 0.39 |
| 10.5 | 8% total (after 8 hours plus 2%) | 23.9 | 0.21 |

Experiment 3
3% Solution of Ovomucine/Alcalase Hydrolysate (DH 23.9, IC50 0.21 mg/ml), pH8, 60° C., Alcalase

| Hydrolyse time total (hours) | Enzyme (%) | DH | ACE inhibition IC50 (mg/ml) |
|---|---|---|---|
| 10.5 | 8% total | 21.2 | 0.25 |
| 13.5 | 10% total | 22.0 | 0.18 |
| 16.5 | 12% total | 21.1 | 0.18 |

Ovomucin/Alcalase Hydrolysate for Animal Study
Summary of Further Hydrolysis of the Ovomucin/Alcalase Hydrolysate
  6 g hydrolysate (Ovomucin/Alcalase hydrolysate, 5 hours) 60° C., pH 8
  120 µl Alcalase
  After 3 hours, 120 µl Alcalase extra
  After 3 hours, 120 µl Alcalase extra
  After 30 minutes the reaction is stopped (15 minutes at 90° C.)
  freeze dried
total hydrolysis time (5+6.5)=11.5 hours
ACE activity: IC50=0.23 mg/ml
Sample has been used in example 8.2.4.1.

Example 3

Initial Egg Protein Hydrolysis Experiments (Prior to Protocol Optimization)

For the hydrolysis experiments ten commercially available enzymes have been used and nine target protein samples. The following enzymes have been used in the hydrolysis experiments (optimal pH, temperature and buffer are given between brackets):

Newlase F (pH 3, T50, formate buffer)
Pepsin 389P (pH3, T50, formate buffer)
Promod 258P (pH5.5, T45, acetate buffer)
Promod 184P (pH6, T50, Bis-Tris buffer)
Flavourzyme (pH7, T50, phosphate buffer)
Alcalase (pH8, T60, Tris buffer)
PEM (pH8, T50, Tris buffer)
PTN (pH8, T50, Tris buffer)
Corolase PP (pH8, T50, Tris buffer)
Protex 6L (pH8, T60, Tris buffer)

The following commercially available target protein compositions were used (manufacturer and specification are given between brackets):
  Lysozyme (Belovo, 100% protein)
  Ovotransferrin (Sigma, Aldrich, 81.3% protein)
  Ovomucin (Belovo, 72.3% protein)
  Ovalbumin (Worthington, 75.7% protein)
  Egg Yolk (NIVE, 31.6% protein)
  Egg White 1101 (NIVE, 79.7% protein)
  Egg White 1102 (NIVE, 77.2% protein)
  Ovalbumin (Interchema, 70.8% protein)
  Ovotransferrin (Belovo, 89.5% protein)

The percentage protein was determined according to Kjeldahl (Kjeldahl factor 6.25).
The initial hydrolysis experiments were done in buffer at the optimal pH and Temperature. The protocol was:
  Protein fraction (100 mg protein) was dissolved in 3.3 ml buffer
  Solution was vortexed
  At t=0 a sample was taken (300 µl) and stored in the freezer at −20° C.
  The solution was incubated for 15 minutes at 90° C. in a waterbath (while shaking). This step was not done in the case of lysozyme due to formation of aggregates.
  After cooling down to the desired temperature the enzyme was added (1.8 mg or 1.8 µl; 2% enzyme with respect to protein fraction added)
  After mixing the tube was vortexed
  Solution was incubated for 3 hour while stirred by a magnetic bar; in between the solution was vortexed
  The enzyme was inactivated by incubation at 90° C. for 15 minutes in a waterbath (shaking)
  The pH was determined and the solution was freeze dried and stored at 4° C.

After an initial screening of all target protein-enzyme combinations (results not shown) the most promising samples (i.e., with a IC50 below 0.5 mg/ml) were analysed again. The ACE inhibition results as a function of the protein concentration are given in the next table (Captopril was used in a concentration of 6 ng/ml):

| | Ovalbumin | | | | | | | |
|---|---|---|---|---|---|---|---|---|
| hydrolysate | inhibition (%) | | | | | | | |
| (mg/ml) | Promod 258P | | PEM | | Newlase F | | Alcalase | |
| 2 | 103.0 | 78.2 | 61.0 | 39.1 | 87.8 | 82.5 | 64.4 | 89.2 | 74.8 |
| 1 | 87.5 | 67.0 | 57.3 | 36.3 | 18.2 | 55.9 | 41.3 | 71.9 | 26.4 |
| 0.5 | 48.6 | 57.6 | 51.4 | 27.7 | 31.1 | 45.8 | 24.6 | 55.1 | 15.9 |
| 0.25 | 37.3 | 33.8 | 32.3 | 1.3 | 17.4 | 23.5 | 13.4 | 27.3 | 0.9 |
| 0.125 | 40.7 | 23.2 | 22.8 | −11 | 0.0 | 16.3 | 1.6 | 7.3 | 16.2 |
| 0.0625 | 14.0 | 8.7 | 26.5 | −21 | −6.8 | 3.7 | 0 | 23.4 | 3.1 |
| Captopril | 74.9 | 55.9 | 84.2 | 67.4 | 57.0 | 81.1 | 74.3 | 86.7 | 67.4 |

| Ovotransferrin hydrolysate (mg/ml) | Promod 258P | | PTN | | PEM | | Newlase F | | Protex 6L | |
|---|---|---|---|---|---|---|---|---|---|---|
| 2 | 121 | 104 | 108 | 146 | 97.1 | 63.7 | 64.3* | 46.8* | 97.3 | 88.0 |
| 1 | 85.2 | 86.2 | 80.3 | 84.3 | 69.1 | 73.8 | 96.1 | 83.1 | 76.8 | 70.2 |
| 0.5 | 57.7 | 66.3 | 67.8 | 59.9 | 52.4 | 56.6 | 70.5 | 69.1 | 60.2 | 58.6 |
| 0.25 | 41.1 | 45.1 | 49.8 | 51.0 | 9.8 | 31.8 | 58.6 | 51.6 | 44.4 | 34.4 |
| 0.125 | 40.0 | 18.8 | 28.3 | 37.9 | −6.4 | 23.5 | 33.7 | 50.9 | 30.6 | 19.1 |
| 0.0625 | 18.4 | −1.0 | 19.8 | −9.7 | −19.4 | −10.7 | 26.9 | 28.7 | 13.7 | 12.0 |
| Captopril | 67.2 | 57.0 | 74.9 | 70.9 | — | 70.9 | 84.1 | 75.7 | 75.0 | 66.7 |

*Absorption above 3

| Lysozyme hydrolysate (mg/ml) | Protex 6L | | PEM | | Alcalase | | PTN | |
|---|---|---|---|---|---|---|---|---|
| 2 | 107 | 79.5 | 102.0 | 123.1 | 126.3 | 102.1 | 79.7 | 103.0 |
| 1 | 83.0 | 83.5 | 79.5 | 141.3 | 81.3 | 79.9 | 75.7 | 75.8 |
| 0.5 | 73.9 | 68.7 | 54.7 | 58.0 | 82.1 | 58.1 | 62.4 | 42.0 |
| 0.25 | 65.8 | 58.3 | 49.7 | 49.5 | 63.6 | 36.5 | 52.8 | 18.7 |
| 0.125 | 42.2 | 44.6 | 38.0 | 35.1 | 46.3 | 16.4 | 42.7 | 12.6 |
| 0.0625 | 42.4 | 30.9 | 29.2 | 27.3 | 35.2 | 14.3 | 18.9 | 6.4 |
| Captopril | 78.1 | 67.2 | 43.5 | 55.5 | 76.0 | 82.9 | 70.9 | 82.9 |

| Ovomucin hydrolysate (mg/ml) | Protex 6L | | PTN | | Newlase F | | PEM | | Alcalase | | |
|---|---|---|---|---|---|---|---|---|---|---|---|
| 2 | 90.8 | 65.8 | 74.3 | 48.4 | 59.6 | 49.2 | 73.1 | 78.1 | 88.0 | 81.7 | 86.0 |
| 1 | 87.6 | 65.0 | 65.5 | 50.9 | 45.7 | 49.2 | 51.3 | 62.3 | 66.0 | 67.2 | 69.9 |
| 0.5 | 68.5 | 49.0 | 55.3 | 44.7 | 42.5 | 31.3 | 66.3 | 43.1 | 48.6 | 57.3 | 55.2 |
| 0.25 | 47.8 | 30.5 | 43.8 | 21.0 | 30.6 | 18.6 | 41.1 | 19.6 | 36.1 | 37.1 | 43.8 |
| 0.125 | 31.4 | 16.3 | 19.7 | 16.9 | 65.2 | 9.0 | 13.3 | 9.1 | — | 25.5 | 33.2 |
| 0.0625 | 24.9 | 5.1 | 23.6 | −11.3 | −13.7 | 7.8 | 25.9 | 5.5 | — | 24.0 | 22.0 |
| Captopril | 80.3 | 66.7 | 76.6 | 72.2 | 60.6 | 55.5 | 86.7 | 78.3 | 88.1 | 75.8 | 88.1 |

| Yolk hydrolysate (mg/ml) | rotex 6L | | PTN | | PEM | | Newlase F | | Alcalase | |
|---|---|---|---|---|---|---|---|---|---|---|
| 2 | 105 | 89.9 | 96.9 | 78.1 | 99.7 | 96.6 | 63.6 | 91.9 | 100 | 100 |
| 1 | 64.1 | 92.6 | 75.7 | 59.9 | 69.8 | 64.6 | 69.5 | 80.0 | 97.8 | 141.7 |
| 0.5 | 48.8 | 74.7 | 31.7 | 57.4 | 62.1 | 52.9 | 51.3 | 57.3 | 75.8 | 61.0 |
| 0.25 | 41.3 | 62.7 | 27.6 | 44.3 | 45.3 | 36.6 | 24.1 | 36.1 | 59.1 | 41.9 |
| 0.125 | 26.6 | 37.0 | −10.6 | 21.9 | 28.8 | 52.8 | 21.7 | 18.2 | 45.7 | 25.1 |
| 0.0625 | 15.0 | 22.4 | −38.2 | 3.9 | 15.4 | 25.4 | 15.5 | 21.6 | 30.9 | 6.5 |
| Captopril | 72.2 | 68.8 | 70.5 | 65.8 | 78.9 | 77.9 | 45.3 | 70.7 | 73.3 | 70.7 |

| EggWhite 1101 | | | | | | |
|---|---|---|---|---|---|---|
| hydrolysate | inhibition (%) | | | | | |
| (mg/ml) | Alcalase | | Promod 258P | | Protex 6L | |
| 2 | 96.3 | 124.6 | 89.4 | 132.9 | 60.1 | 92.9 |
| 1 | 66.5 | 71.7 | 77.9 | 78.4 | 63.2 | 62.2 |
| 0.5 | 63.1 | 39.9 | 62.8 | 47.2 | 50.6 | 44.4 |
| 0.25 | 46.5 | 32.1 | 45.0 | 33.9 | 31.3 | 33.3 |
| 0.125 | 34.2 | 12.8 | 40.3 | 36.2 | 20.2 | 23.0 |
| 0.0625 | 19.6 | 10.7 | 27.9 | 20.0 | 17.0 | 11.9 |
| Captopril | 78.4 | 84.0 | 77.0 | 84.0 | 78.1 | 67.2 |

| EggWhite 1102 | | | | | | |
|---|---|---|---|---|---|---|
| hydrolysate | inhibition (%) | | | | | |
| (mg/ml) | Alcalase | | Promod 258P | | Protex 6L | |
| 2 | 86.3 | 65.8 | 91.3 | 76.8 | 60.2 | 71.8 |
| 1 | 76.9 | 67.0 | 75.0 | 61.9 | 58.4 | 66.0 |
| 0.5 | 58.8 | 48.1 | 62.0 | 42.7 | 47.0 | 49.2 |
| 0.25 | 43.0 | 23.3 | 42.8 | 19.5 | 33.2 | 41.7 |
| 0.125 | 36.4 | 16.7 | 30.8 | 4.6 | 24.7 | 19.0 |
| 0.0625 | 18.2 | 2.4 | 33.2 | −10.3 | 16.3 | 4.9 |
| Captopril | 78.4 | 61.9 | 73.3 | 61.9 | 75.0 | 68.8 |

An analysis of the results shown above is presented in the next table. The target protein—enzyme combinations are scored on ACE inhibiting activity, the repeatability of this inhibition and on appearance (which is also a measure of the ease with which the hydrolysate can be handled).

Protein-enzyme combinations with more than 50% ACE inhibition at 0.5 mg/ml:

| Source | Enzyme | ACE inhibition (% inhibition) (3 to 6 values per sample) | | | | | | ap[#] | 1 | 2 | 3 | Total score |
|---|---|---|---|---|---|---|---|---|---|---|---|---|
| Egg-white | Alcalase | 52 | 54 | 63 | 40 | 59 | 40 | ts | + | o | + | ++ |
| | Promod258P | 55 | 52 | 63 | 47 | 62 | 43 | p | + | o | o | + |
| Egg yolk | Alcalase | 68 | 76 | 61 | | | | m | ++ | − | + | ++ |
| | Protex6L | 62 | 49 | 75 | | | | m, p | ++ | + | o | +++ |
| | PEM | 58 | 62 | 53 | | | | m, p | + | + | o | ++ |
| | NewlaseF | 57 | 51 | 57 | | | | m, p | + | + | o | ++ |
| Ovalbumin | Promod258P | 53 | 49 | 58 | | | | ts | + | + | + | +++ |
| Ovotransferrin | NewlaseF | 70 | 71 | 69 | | | | s | ++ | + | ++ | +++++ |
| | Promod258P | 62 | 58 | 66 | | | | a | ++ | + | o | +++ |
| | PTN | 64 | 68 | 60 | | | | s | ++ | + | ++ | +++++ |
| | PEM | 55 | 52 | 57 | | | | s | + | + | ++ | ++++ |
| | Protex6L | 59 | 60 | 59 | | | | p | + | + | o | ++ |
| Ovomucin | PEM | 53 | 66 | 43 | 49 | | | s | + | − | ++ | ++ |
| | Alcalase | 56 | 57 | 55 | | | | s | + | + | ++ | ++++ |
| | PTN | 50 | 55 | 45 | | | | ts | + | o | + | ++ |
| | Protex6L | 59 | 69 | 49 | | | | t, b | + | − | o | o |
| Lysozyme | Alcalase | 70 | 82 | 58 | | | | s | ++ | − | ++ | +++ |
| | Protex6L | 71 | 74 | 69 | | | | p | ++ | + | o | +++ |
| | PEM | 56 | 55 | 58 | | | | s | + | + | ++ | ++++ |
| | PTN | 52 | 62 | 42 | | | | s | + | − | ++ | ++ |

[#]appearance: s = solution, p = particles, m = milky, a = aggregates, ts = turbid solution
1: ACE inhibition >60% is ++; between 50-60% is +
2: Difference between highest and lowest value <10% is +; between 10-20% is 0; >20% is −
3: Solubility: solution is ++; turbid solution is +; milky is +; particles is 0; aggregates is 0

Any target protein of the table above (especially in combination with the enzyme(s) indicated or with enzyme(s) having equivalent activity) is suitable for making a target protein hydrolysate and a food supplement/product (comprising such hydrolysate in suitable amounts) with blood pressure lowering activity.

Based on the scores the following protein-enzyme combinations were ranked as the best with respect to in vitro ACE inhibiting activity after hydrolysis of the proteins in buffer. To this end the scores per category were summed for each target protein-enzyme combination and the following ranking was obtained:

Best Ten Target Protein-Enzyme Combinations

| Score | Source | Enzyme |
|---|---|---|
| +++++ | Ovotransferrin | NewlaseF |
| | Ovotransferrin | PTN |
| ++++ | Ovomucin | Alcalase |
| | Ovotransferrin | PEM |
| | Lysozyme | PEM |
| +++ | Egg Yolk | Protex6L |
| | Ovalbumin | Promod258P |
| | Ovotransferrin | Promod258P |
| | Lysozyme | Alcalase |
| | Lysozyme | Protex6L |

Analysis of the number of proteins and enzymes occurring in the set of best combinations shows the following distribution:

| Proteins | # | Enzymes | # |
|---|---|---|---|
| Ovotransferrin | 4 | Alcalase | 2 |
| Lysozyme | 3 | Promod258P | 2 |
| Ovomucin | 1 | PEM | 2 |
| Egg yolk | 1 | Protex6L | 2 |
| Ovalbumin | 1 | PTN | 1 |
| Egg white | 0 | NewlaseF | 1 |

It appeared that certain enzymes are less effective in releasing bioactive peptides from target proteins, such as Pepsin, Promod184P, Flavourzyme and CorolasePP. It was interesting to note that both CorolasePP and Flavourzyme are enzymes that give very high amounts of free amino acids (11.5-13.0%) due to their exoprotease activity. In these hydrolysates rather free amino acids than short peptides are formed, resulting in low concentrations of ACE-inhibiting peptides. Without limiting the scope of the invention, it is proposed that enzymes releasing relatively high amounts of free amino acids compared to amounts of di- and tri-peptides are less suitable. Promod258P, which is also a mixture of endo- and exoproteases and is known to give quite a lot of free amino acids (9.3%) is a satisfactory enzyme for the production of ACE-inhibiting hydrolysates.

Example 4

Hydrolysis in Water and Optimization of the Hydrolysis Protocol

Hydrolysis was performed in water in view of commercial applications, where the use of buffers is less desired. Consumer products should not contain additional salt components if not explicitly necessary and, therefore, the optimal buffer conditions for each enzyme was replaced by water. The pH of the solution during the reaction was adjusted by addition of NaOH or HCl.

Incubation time of enzymes with target proteins was also further optimised. The initial hydrolysis protocol was identical to the protocol in buffer above, however, after 3 hours an additional amount of enzyme (again 2% w/w) was used to further hydrolyse the protein. Samples were taken every hour. Fractions were tested in the ACE inhibition assay and the results are shown in the next table.

| Protein | Enzyme | Hydr. (mg/ml) | Inhibition (%) | | | | | |
|---|---|---|---|---|---|---|---|---|
| | | | 1 hr | 2 hr | 3 hr | 4 hr | 5 hr | 6 hr |
| Ovotransferrin | NewlaseF | 1 | 40.9 | 67.4 | 56.2 | 88.2 | 87.9 | 81.3 |
| | | 0.5 | 66.8 | 62.7 | 72.4 | 67.1 | 76.8 | 64.5 |
| | | 0.25 | 53.0 | 41.4 | 54.0 | 56.8 | 63.7 | 49.3 |
| | | 0.125 | 46.2 | 33.2 | 42.6 | 40.5 | 42.9 | 47.4 |
| | PTN | 1 | 14.3 | 18.5 | 28.4 | 87.1 | 92.1 | 89.1 |
| | | 0.5 | 9.9 | 11.5 | 28.9 | 75.1 | 80.9 | 81.5 |
| | | 0.25 | 17.2 | 10.1 | 10.0 | 59.4 | 67.2 | 62.4 |
| | | 0.125 | 19.0 | 8.2 | 16.7 | 38.8 | 53.0 | 38.2 |
| | Promod258P | 1 | 89.5 | 95.6 | 96.9 | 94.5 | 105 | 91.9 |
| | | 0.5 | 85.5 | 83.7 | 75.7 | 84.0 | 81.0 | 78.0 |
| | | 0.25 | 62.4 | 69.2 | 64.6 | 73.8 | 69.5 | 68.0 |
| | | 0.125 | 60.3 | 58.9 | 54.0 | 59.7 | 57.8 | 53.5 |
| Ovomucin | Alcalase | 1 | 25.0 | 35.0 | 30.5 | 72.3 | 76.0 | 86.0 |
| | | 0.5 | 17.2 | 17.0 | 22.4 | 62.8 | 60.7 | 74.9 |
| | | 0.25 | 9.6 | 23.9 | 15.6 | 42.4 | 47.6 | 58.3 |
| | | 0.125 | 7.0 | 22.0 | 11.3 | 30.8 | 34.7 | 47.8 |
| | PTN | 1 | 23.0 | 35.3 | 41.5 | 73.7 | 79.2 | 64.3 |
| | | 0.5 | 20.6 | 24.7 | 31.3 | 52.3 | 57.9 | 59.5 |
| | | 0.25 | 12.9 | 15.8 | 22.6 | 44.4 | 51.0 | 41.3 |
| | | 0.125 | 7.4 | 13.8 | 14.4 | 41.6 | 44.0 | 23.2 |
| Lysozyme | Alcalase | 1 | 79.8 | 91.6 | 90.9 | 89.9 | 78.8 | 92.1 |
| | | 0.5 | 73.0 | 73.3 | 77.1 | 77.6 | 73.2 | 54.9 |
| | | 0.25 | 65.6 | 61.5 | 64.7 | 63.7 | 68.9 | 44.2 |
| | | 0.125 | 32.6 | 41.6 | 49.3 | 47.2 | 53.7 | 30.2 |
| | Protex6L | 1 | 78.2 | 92.0 | 93.0 | 91.4 | 96.3 | 97.1 |
| | | 0.5 | 77.0 | 80.0 | 83.1 | 85.6 | 85.1 | 83.6 |
| | | 0.25 | 61.3 | 70.4 | 66.2 | 68.7 | 75.4 | 70.4 |
| | | 0.125 | 49.6 | 54.5 | 50.1 | 55.8 | 65.3 | 61.9 |
| | PEM | 1 | 77.0 | 95.3 | 89.3 | 88.2 | 88.3 | 83.8 |
| | | 0.5 | 63.5 | 78.1 | 78.9 | 77.4 | 86.7 | 76.6 |
| | | 0.25 | 41.8 | 75.3 | 65.0 | 69.9 | 66.7 | 62.0 |
| | | 0.125 | 50.9 | 48.0 | 50.5 | 53.3 | 58.4 | 53.1 |
| Egg Yolk | Alcalase | 1 | 73.8 | 67.8 | 74.5 | 77.7 | 85.6 | 79.1 |
| | | 0.5 | 53.4 | 47.4 | 62.1 | 62.6 | 68.8 | 61.2 |
| | | 0.25 | 34.2 | 42.1 | 52.0 | 45.5 | 53.9 | 32.0 |
| | | 0.125 | 26.1 | 19.2 | 29.3 | 27.2 | 45.2 | 17.1 |
| | Protex6L | 1 | 79.5 | 73.2 | 79.2 | 82.6 | 89.4 | 90.6 |
| | | 0.5 | 50.2 | 59.5 | 65.1 | 68.8 | 71.6 | 72.5 |
| | | 0.25 | 35.1 | 45.7 | 47.3 | 55.5 | 59.3 | 56.8 |
| | | 0.125 | 18.3 | 36.1 | 32.1 | 38.3 | 49.0 | 41.6 |
| | NewlaseF | 1 | 58.5 | 67.9 | 72.3 | 63.4 | 78.1 | 79.2 |
| | | 0.5 | 53.0 | 53.4 | 60.5 | 62.8 | 69.4 | 65.0 |
| | | 0.25 | 32.1 | 41.2 | 44.8 | 47.5 | 58.6 | 46.0 |
| | | 0.125 | 25.3 | 29.4 | 31.0 | 35.4 | 42.6 | 29.0 |
| Egg White 1101 | Alcalase | 1 | 66.4 | 67.2 | 62.7 | 77.4 | 82.3 | 77.9 |
| | | 0.5 | 38.7 | 43.6 | 53.3 | 55.2 | 70.0 | 60.8 |
| | | 0.25 | 28.1 | 23.1 | 32.6 | 38.9 | 49.0 | 45.9 |
| | | 0.125 | 22.0 | 11.8 | 12.3 | 21.5 | 38.9 | 18.6 |

The rows with protein concentration of 0.5 mg/ml has been shaded as relevant reference. If the percentage inhibition for this value is 50% or higher the hydrolysate is likely to have antihypertensive activity in vivo.

The optimal hydrolysis time for the egg white and egg yolk samples is approximately 5 hours, giving IC50 values between 0.15 and 0.25 mg/ml. For the purified proteins, i.e., lysozyme, ovotransferrin and ovomucin the optimal hydrolysis times are between 4 and 5 hours and IC50 values (as calculated from the data in the Table) range from below 0.1 mg/ml (lysozyme and ovotransferrin) to 0.3 mg/ml (ovomucin).

Example 5

In Vitro Digestion Simulation Experiments 5.1

With the protein-enzyme combinations an in vitro digestion simulation was performed to study the possible effect of the endogenous digestive system. If the ACE inhibiting activity of an in vitro optimised hydrolysate would be negatively influenced by the endogenous proteolytic enzymes, the optimisation should be adapted to cope with this. Therefore, the following protocol was used:

A 4% protein (hydrolysate) sample solution is made
The pH is set to 2
From a pepsin solution of 10 mg/ml an amount is added to a ratio of 1/250 (w/w)
The solution is incubated for 2 hours at 37° C. in a waterbath under shaking
The pH is set to 6.5
From a solution containing 10 mg/ml trypsin and chymotrypsin, respectively, amounts are added to a ratio of 1/250 (w/w)
The solution is incubated for 2.5 hours at 37° C. in a waterbath under shaking
The enzymes are inactivated by incubation at 90° C. for 15 minutes
Samples are freeze dried and stored at 4° C.

This protocol was performed with the hydrolysed samples of time points 6 hours. The results (percentage inhibition) are shown in the next table and the rows with a level of 0.5 mg/ml hydrolysate have a shaded background.

| Protein | Enzyme | Hydr. (mg/ml) | Inhibition (%) | | |
|---|---|---|---|---|---|
| | | | 6 hr hydr. (exp. 1) | 6 hr hydr. (exp. 2) | 6 hr hydr. + dig. sim. |
| Ovotransferrin | NewlaseF | 1 | 81.3 | 80.9 | 109 |
| | | 0.5 | 64.5 | 75.7 | 76.4 |
| | | 0.25 | 49.3 | 65.3 | 75.5 |
| | | 0.125 | 47.4 | 65.0 | 66.1 |
| | PTN | 1 | 89.1 | 84.8 | 84.9 |
| | | 0.5 | 81.5 | 76.3 | 78.6 |
| | | 0.25 | 62.4 | 58.6 | 65.3 |
| | | 0.125 | 38.2 | 53.0 | 47.8 |
| | Promod258P | 1 | 91.9 | 91.4 | 85.1 |
| | | 0.5 | 78.0 | 71.4 | 77.8 |
| | | 0.25 | 68.0 | 69.0 | 68.2 |
| | | 0.125 | 53.5 | 53.9 | 59.5 |
| Ovomucin | Alcalase | 1 | 86.0 | 74.1 | 80.7 |
| | | 0.5 | 74.9 | 61.6 | 61.3 |
| | | 0.25 | 58.3 | 45.6 | 50.2 |
| | | 0.125 | 47.8 | 30.6 | 30.7 |
| | PTN | 1 | 64.3 | 74.9 | 73.0 |
| | | 0.5 | 59.5 | 51.9 | 64.0 |
| | | 0.25 | 41.3 | 51.6 | 52.2 |
| | | 0.125 | 23.2 | 41.6 | 43.9 |
| Lysozyme | Alcalase | 1 | 92.1 | 106 | 98.1 |
| | | 0.5 | 54.9 | 88.1 | 86.3 |
| | | 0.25 | 44.2 | 78.6 | 76.5 |
| | | 0.125 | 30.2 | 69.1 | 69.1 |
| | Protex6L | 1 | 97.1 | 84.7 | 108 |
| | | 0.5 | 83.6 | 83.3 | 85.1 |
| | | 0.25 | 70.4 | 78.2 | 75.8 |
| | | 0.125 | 61.9 | 54.0 | 64.1 |
| | PEM | 1 | 83.8 | 97.4 | 91.3 |
| | | 0.5 | 76.6 | 88.7 | 84.7 |
| | | 0.25 | 62.0 | 80.3 | 77.2 |
| | | 0.125 | 53.1 | 72.1 | 68.1 |
| Egg Yolk | Alcalase | 1 | 79.1 | 80.1 | 91.8 |
| | | 0.5 | 61.2 | 77.5 | 77.8 |
| | | 0.25 | 32.0 | 58.7 | 66.0 |
| | | 0.125 | 17.1 | 44.9 | 57.1 |
| | Protex6L | 1 | 90.6 | 101 | 81.8 |
| | | 0.5 | 72.5 | 74.6 | 73.8 |
| | | 0.25 | 56.8 | 59.6 | 59.4 |
| | | 0.125 | 41.6 | 45.5 | 44.4 |
| | NewlaseF | 1 | 79.2 | 71.0 | 74.8 |
| | | 0.5 | 65.0 | 55.1 | 58.0 |
| | | 0.25 | 46.0 | 36.9 | 41.6 |
| | | 0.125 | 29.0 | 12.3 | 22.3 |
| Egg White 1101 | Alcalase | 1 | 77.9 | 80.6 | 74.8 |
| | | 0.5 | 60.8 | 58.6 | 61.5 |
| | | 0.25 | 45.9 | 36.6 | 46.8 |
| | | 0.125 | 18.6 | 25.5 | 30.1 |

As judged from the 0.5 mg/ml points for none of the target protein-enzyme combinations the ACE inhibitory potential is substantially changed after in vitro digestion simulation. The overall results, including all IC50 values at the various time points are shown in the next table. Three different studies are summarized: 1. Screening after 3 hours of hydrolysis in buffer; 2. Optimisation of hydrolysis in water; 3. Digestion simulation on the 6 hours hydrolysed samples.

| Protein/ Enzyme | IC50 (mg/ml) | | | | | | | | |
|---|---|---|---|---|---|---|---|---|---|
| | Screening (3 hr hydr. in buffer) | Optimisation (hydrolysis in water) | | | | | | Digestion Simulation | |
| | | 1 hr | 2 hr | 3 hr | 4 hr | 5 hr | 6 hr | before | after |
| OT + NewF | 0.19 | 0.36 | 0.33 | 0.19 | 0.20 | 0.16 | 0.20 | 0.03 | 0.09 |
| OT + PTN | 0.26 | — | 293 | 2.93 | 0.19 | 0.10 | 0.18 | 0.12 | 0.13 |
| OT + Pr258 | 0.29 | 0.09 | 0.08 | 0.12 | 0.07 | 0.10 | 0.10 | 0.11 | 0.06 |
| OM + Alc | 0.38 | 23 | 2.6 | 12.2 | 0.45 | 0.39 | 0.20 | 0.43 | 0.39 |
| OM + PTN | 0.59 | 34.0 | 5.7 | 2.8 | 0.41 | 0.31 | 0.56 | 0.34 | 0.28 |
| Lys + Alc | 0.25 | 0.21 | 0.17 | 0.13 | 0.14 | 0.08 | 0.30 | 0.05 | 0.04 |
| Lys + Pr6L | 0.16 | 0.13 | 0.09 | 0.12 | 0.09 | 0.05 | 0.07 | 0.09 | 0.07 |
| Lys + PEM | 0.27 | 0.24 | 0.12 | 0.12 | 0.09 | 0.08 | 0.11 | 0.02 | 0.02 |
| Yolk + Alc | 0.23 | 0.40 | 0.46 | 0.29 | 0.31 | 0.18 | 0.39 | 0.16 | 0.09 |
| Yolk + Pr6L | 0.27 | 0.41 | 0.29 | 0.27 | 0.21 | 0.15 | 0.18 | 0.17 | 0.16 |
| Yolk + NewF | 0.38 | 0.54 | 0.40 | 0.32 | 0.31 | 0.18 | 0.18 | 0.44 | 0.37 |
| White + Alc | 0.41 | 0.57 | 0.58 | 0.52 | 0.38 | 0.23 | 0.34 | 0.35 | 0.30 |

5.2
Another experiment was carried out to study the influence of in vitro digestion simulation on hydrolysates of egg yolk and egg white target proteins.
D=in vitro digested simulation
Y+Alc=hydrolysate of Egg Yolk—Alcalase
Yolk D=whole Egg Yolk, digested (in vitro simulation)
Y+Alc D=hydrolysate of Egg Yolk—Alcalase followed by digestion (in vitro simulation)
EW+Alc=hydrolysate of Egg White—Alcalase
Egg White D=whole Egg White, digested (in vitro simulation)
EW+Alc D=hydrolysate of Egg White—Alcalase followed by digestion (in vitro simulation)

| hydrolysaat conc. (mg/ml) | % inhibition Y + Alc | % inhibition Yolk D | % inhibition Y + Alc D |
|---|---|---|---|
| ½ | 25.9 | 42.0 | 38.2 |
| ⅙ | 11.4 | 14.2 | 19.8 |
| 1/18 | 4.6 | 4.6 | 7.7 |
| 1/54 | 0.4 | −2.6 | −2.3 |
| captopril | 33.6 | 87.0 | 88.0 |

| hydrolysaat conc. (mg/ml) | % inhibition EW + Alc | % inhibition Egg White D | % inhibition EW + Alc D |
|---|---|---|---|
| ½ | 53.1 | 56.4 | 54.0 |
| ⅙ | 21.1 | 26.4 | 31.4 |
| 1/18 | 13.2 | 9.8 | 10.0 |
| 1/54 | 9.7 | 3.1 | 0.1 |
| captopril | 33.6 | 87.0 | 88.0 |

As can be seen, the in vitro digestion simulation does not change the ACE inhibiting activity of the hydrolysates.
Lyz+Alc=hydrolysate Lysozyme—Alcalase
Lyz+PEM=hydrolysate Lysozyme—PEM
Lyz D=in vitro digestion simulation of Lysozyme (not pre-hydrolysed)
Lyz+Alc D=hydrolysate (Lysozyme—Alcalase) followed by in vitro digestion simulation
OM+Alc=hydrolysate Ovomucin—Alcalase
OM+PTN=hydrolysate Ovomucin—PTN
OM D=in vitro digestion simulation of Ovomucin (not pre-hydrolysed)
OM+Alc D=hydrolysate (Ovomucin—Alcalase) followed by in vitro digestion simulation
OT+NF=hydrolysate Ovotransferrin—NewlaseF
OT+Pr258P=hydrolysate Ovotransferrin—Promod258P
OT D=in vitro digestion simulation of Ovotransferrin (not pre-hydrolysed)
OT+Alc D=hydrolysate (Ovotransferrin—Promod258P) followed by in vitro digestion simulation

| hydrolysaat conc. (mg/ml) | % inhibition Lyz + Alc | % inhibition Lyz + PEM | % inhibition Lyz D | % inhibition Lyz + Alc D |
|---|---|---|---|---|
| ½ | 76.0 | 73.2 | 76.4 | 79.0 |
| ⅙ | 54.6 | 51.8 | 53.3 | 54.5 |
| 1/18 | 39.6 | 39.3 | 32.7 | 39.8 |
| 1/54 | 24.3 | 21.5 | 15.6 | 17.1 |
| captopril | 67.0 | 67.0 | 88.0 | 88.0 |

| hydrolysaat conc. (mg/ml) | % inhibition OM + Alc | % inhibition OM + PTN | % inhibition OM D | % inhibition OM + Alc D |
|---|---|---|---|---|
| ½ | 44.1 | 38.4 | 49.9 | 55.2 |
| ⅙ | 12.6 | 13.5 | 24.5 | 24.6 |
| 1/18 | 4.7 | 3.9 | 12.8 | 7.0 |
| 1/54 | 2.5 | −8.3 | −0.6 | −4.0 |
| captopril | 52.4 | 52.4 | 87.0 | 85.1 |

| hydrolysaat conc. (mg/ml) | % inhibition OT + NF | % inhibition OT + Pr258P | % inhibition OT D | % inhibition OT + Pr258P D |
|---|---|---|---|---|
| ½ | 53.3 | 74.4 | 57.6 | 80.1 |
| ⅙ | 31.9 | 53.4 | 33.6 | 54.7 |
| 1/18 | 8.9 | 29.2 | 14.6 | 29.8 |
| 1/54 | −2.5 | 14.4 | 9.2 | 11.3 |
| captopril | 43.7 | 43.7 | 87.0 | 85.1 |

The digestion simulation does not negatively or positively influence the ACE inhibiting activity of the resulting hydrolysate. Only hydrolysis of ovotransferrin (OT) adds positively to the ACE inhibiting activity.

Overall, in vitro digestion simulation does not positively or negatively change the ACE inhibiting properties of egg protein hydrolysates. This implies that the digestive activities in the subject do not change the ACE inhibitory activity of the hydrolysates. In vivo confirmation of this is, however, required.

5.3
Study of the influence of two different incubation times for pepsin in the in vitro digestion.

The in vitro digestion studies were repeated with two incubation times for pepsin, i.e., 30 and 120 minutes (D30 and D120), representing a short and a long residence time in the stomach, respectively. Incubation time for the gut simulation was unchanged, i.e., 150 minutes.

In addition, the original proteins and protein fractions (not pre-hydrolysed, nor in vitro digested) were tested in the ACE inhibition assay to assess possible background activity of these proteins.

| Yolk | Yolk-D30 | Yolk-D120 | Yolk + Alc | Y + Alc-D30 | Y + Alc-D120 | conc. (mg/ml) |
|---|---|---|---|---|---|---|
| −7.8 | 37.5 | 45.0 | 33.1 | 40.0 | 44.0 | 0.500 |
| 3.1 | 12.2 | 16.0 | 17.6 | 20.7 | 21.6 | 0.167 |
| 8.3 | 9.0 | 5.9 | 9.5 | 7.3 | 8.1 | 0.056 |
| 10.1 | 1.8 | −5.1 | 13.3 | −1.2 | 2.7 | 0.019 |

| Egg White | EW-D30 | EW-D120 | EW + Alc | EW + Alc-D30 | EW + Alc-D120 | conc. (mg/ml) |
|---|---|---|---|---|---|---|
| 7.9 | 43.6 | 48.9 | 56.8 | 46.7 | 56.9 | 0.500 |
| 4.2 | 17.9 | 20.6 | 28.4 | 25.6 | 27.8 | 0.167 |
| 10.2 | 7.3 | 9.5 | 21.7 | 11.3 | 20.3 | 0.056 |
| 4.6 | 4.0 | −1.0 | 11.8 | 4.6 | 9.9 | 0.019 |

-continued

| Lys UM | Lys D30 | Lys D120 | Lys + Alc | Lys + A D30 | Lys + A D120 | conc. (mg/ml) |
|---|---|---|---|---|---|---|
| 2.6 | 71.1 | 78.2 | 78.2 | 79.1 | 80.5 | 0.500 |
| -4.7 | 55.0 | 61.4 | 50.4 | 58.8 | 56.9 | 0.167 |
| 1.3 | 32.1 | 40.4 | 32.6 | 31.3 | 32.4 | 0.056 |
| 0.1 | 16.5 | 17.9 | 24.5 | 14.8 | 16.5 | 0.019 |

| Lys UM | Lys D30 | Lys D120 | Lys + PEM | Lys + P D30 | Lys + P D120 | conc. (mg/ml) |
|---|---|---|---|---|---|---|
| 2.6 | 71.1 | 78.2 | 79.1 | 74.2 | 76.3 | 0.500 |
| -4.7 | 55.0 | 61.4 | 59.0 | 54.7 | 59.3 | 0.167 |
| 1.3 | 32.1 | 40.4 | 38.1 | 32.4 | 39.4 | 0.056 |
| 0.1 | 16.5 | 17.9 | 18.8 | 20.7 | 22.0 | 0.019 |

| OT-UM | OT-D30 | OT-D120 | OT + Pr258P | OT + P-D30 | OT + P-D120 | conc. (mg/ml) |
|---|---|---|---|---|---|---|
| -0.3 | 53.6 | 68.4 | 73.6 | 74.4 | 75.6 | 0.500 |
| 0.7 | 32.7 | 44.5 | 50.7 | 48.3 | 51.3 | 0.167 |
| -4.1 | 12.1 | 12.4 | 28.1 | 30.4 | 31.0 | 0.056 |
| 0.7 | 7.6 | 7.0 | 15.6 | 10.3 | 12.2 | 0.019 |

| OM-UM | OM-D30 | OM-D120 | OM + Alc | OM + A-D30 | OM + A-D120 | conc. (mg/ml) |
|---|---|---|---|---|---|---|
| 2.1 | 47.1 | 51.8 | 16.0 | 50.0 | 54.3 | 0.500 |
| 2.2 | 21.5 | 26.5 | 7.7 | 23.3 | 30.0 | 0.167 |
| 5.2 | 8.2 | 9.6 | -0.3 | 9.6 | 15.0 | 0.056 |
| -0.4 | 4.0 | 2.1 | 2.5 | 5.6 | 2.3 | 0.019 |

From the above it is concluded that the original (nonhydrolyzed and non-digested) proteins (column 1) do not possess ACE inhibiting activity.

As there is not much difference between the ACE inhibitory activity of hydrolysates that have been treated with pepsin for 30 minutes as compared to those treated for 120 minutes it seems that residence time in the stomach is not influencing the protein hydrolysate properties.

Example 6

Comparison of Egg White Powder and Fresh Starting Material

The objective of this experiment was to determine whether egg white powder resulted in a hydrolysate with different inhibitory activity than fresh egg white starting material. Commercially available egg white powder was compared with freshly prepared egg white and tested for ACE inhibitory activity to study the influence of freshness.

The assay conditions were:

Number of experiments: 3

The commercial available EW 1101 product was a lysozyme depleted product and for this experiment was enriched with 3.4% lysozyme (Belovo)

Controls: No pepsin/chymotrypsin/trypsin digestion (only hydrolysis with alcalase)

D30/D120:30'/120' pepsin digestion, followed by 2.5 h α-chymotrypsin/trypsin digestion at pH 6.5, 37° C.

The ACE inhibitory activity (IC50 in mg/ml) was determined:

| Sample | IC50 (mg/ml) | | |
|---|---|---|---|
| | Controls | D30 | D120 |
| EW1101 + lysozyme/Alcalase | 0.38 | 0.41 | 0.53 |
| Fresh egg white/Alcalase | 0.51 | 0.42 | 0.58 |
| Egg yolk/Alacalase | 0.54 | 0.59 | 0.93 |

The result showed that both dried egg white powder and fresh egg white have significant ACE inhibitory activity.

Example 7

Activity of Soluble and Solid Fractions of Hydrolysate

The objective was to determine the ACE inhibitory activity in the soluble and insoluble fractions of hydrolysates. To this end, egg white, lysozyme and ovomucin were hydrolysed by alcalase and the resulting hydrolysates were fractionated by centrifugation (15 min; 4,500×g). The pellet and supernatant fractions were freeze-dried separately.

On a dry weight basis the pellet and supernatant fractions were divided as follows:

| Hydrolysate | Pellet (%) | Supernatant (%) |
|---|---|---|
| EW/Alcalase | 15.2 | 84.8 |
| | 15.9 | 84.1 |
| Lysozyme/Alcalase | 1.5 | 98.5 |
| | 1.4 | 98.6 |
| Ovomucin/Alcalase | 27.2 | 72.8 |
| | 24.3 | 75.7 |

The ACE inhibitory activity was determined and compared to the activity of whole hydrolysates that were freeze-dried directly after hydrolysis.

| Hydrolysate | Inhibition (%) | | | | | |
|---|---|---|---|---|---|---|
| | EW1101/ Alcalase | | Lysozyme/ Alcalase | | Ovomucin/ Alcalase | |
| (mg/ml) | pellet | sup | pellet | sup | pellet | sup |
| 0.50 | 39.4 | 60.6 | 59.6 | 68.3 | 22.9 | 47.4 |
| 0.17 | 27.5 | 36.1 | 43.6 | 53.7 | 10.5 | 42.1 |
| 0.06 | 16.8 | 13.9 | 22.3 | 32.5 | −3.0 | 16.2 |
| 0.02 | 3.5 | 8.5 | 5.4 | 23.6 | −5.2 | −6.6 |
| IC50 (mg/ml) | 1.43 | 0.31 | 0.27 | 0.15 | 4.89 | 0.41 |
| Reference[1] | 45.9 | 45.9 | 45.9 | 45.9 | 45.9 | 45.9 |

[1] A standard reference of egg white sample was measured in each plate (Egg White 1101/Alcalase, produced 25-9-2003; solution of 0.5 mg/ml

| Whole hydrolysate[1] | EW/Alcalase | Lysozyme/Alcalase | Ovomucin/ Alcalase |
|---|---|---|---|
| IC50 (mg/ml) | 0.58 | 0.12 | 0.32 |

[1] no centrifugation

In two cases, i.e., EW1101 and Ovomucin, the separation of pellet and supernatant resulted in increased ACE inhibitory activity of the supernatant. The differences with the whole, non-centrifuged hydrolysates were less than a factor two.

Also, from the insoluble fraction of ovomucin/alcalase hydrolysate substantial ACE inhibitory activity could be released from the pellet after in vitro digestion simulation under the indicated conditions:

| Hydrolysate | | IC50 (mg/ml) | IC50 (mg/ml) without digestion simulation | IC50 (mg/ml) after digestion simulation with pepsin, chymotrypsin, trypsin | | |
|---|---|---|---|---|---|---|
| | | | | 0 min pepsin | 30 min pepsin | 120 min pepsin |
| Egg white - alcalase | | 0.58 | pellet | 1.40 | 1.80 | 0.64 | 0.69 |
| | | | Supern. | 0.38 | 0.55 | 0.62 | 0.74 |
| Ovomucin - alcalase | | 0.32 | pellet | 6.40 | 1.37 | 0.77 | 0.61 |
| | | | Supern. | 0.49 | 0.36 | 0.40 | 0.41 |

The activity present in the pellet should if possible be included in the final food product.

Example 8

In Vivo Experiments 8.1 First In Vivo Experiment
8.1.1 First Large Scale Hydrolysate Preparation To have large batches available for in vivo experiments hydrolyses were performed on a 20 to 25 gram scale. The following hydrolysates were prepared:
1. Lysozyme/Alcalase (Lys+Alc)
2. Lysozyme/PEM (Lys+PEM)
3. Ovomucin/Alcalase (OM+Alc)
4. Ovotransferrin/Promod 258P (OT+Pr258P)
5. Egg Yolk/Alcalase (Y+Alc)
6. Egg White/Alcalase (EW+Alc)

The ACE inhibiting activity of these large scale hydrolysates was tested and appeared to be very similar to that of the small scale hydrolysates tested before:

| Hydrolyses on a 850 ml scale | | | | | | |
|---|---|---|---|---|---|---|
| Y + Alc | EW + Alc | Lys + Alc | OM + Alc | OT + Pr258P | Lys + PEM | conc. (mg/ml) |
| 31.6 | 42.3 | 80.4 | 18.4 | 66.8 | 82.4 | 0.500 |
| 15.8 | 19.1 | 58.0 | 10.5 | 50.5 | 54.2 | 0.167 |
| 11.0 | 14.0 | 38.2 | 8.8 | 27.9 | 28.0 | 0.056 |
| 6.0 | 9.2 | 22.0 | 4.8 | 13.1 | 15.2 | 0.019 |

8.1.2 Second Large Scale Experiment

Another large scale experiments was performed to produce hydrolysates for the in vivo SHR studies. A summary of ACE inhibitory activity of the various batches and samples is given in the next table. The samples were tested in duplicates.

| Hydrolysate (mg/ml) | Inhibition (%) | | | | | | |
|---|---|---|---|---|---|---|---|
| | EW1101/ Alcalase | | Lysozym/ Alcalase | | Ovomucin/ Alcalase | | Ovotransferrin/ NewF |
| | 1st batch | 2nd batch | 1st batch | 2nd batch | 1st batch | 2nd batch | 1st batch |
| 0.50 | 52.2 | 48.7 | 80.1 | 81.9 | 54.1 | 60.6 | 58.6 |
| 0.17 | 25.5 | 22.6 | 52.8 | 53.5 | 25.6 | 32.4 | 44.7 |
| 0.06 | 6.6 | 11.5 | 39.3 | 35.6 | 19.5 | 18.4 | 20.6 |
| 0.02 | 4.3 | 5.7 | 20.4 | 18.0 | 12.0 | 9.9 | 8.4 |
| IC50 | 0.52 | 0.58 | 0.11 | 0.12 | 0.47 | 0.32 | 0.27 |
| Reference[1] | 47 | 45.5 | 47 | 45.5 | 47 | 45.9 | 47 |

[1] A standard reference of egg white sample was measured in each plate (Egg White 1101/Alcalase, produced 25-9-2003; solution of 0.5 mg/ml).

From the above table it is obvious that there is a high level of repeatability in IC50 values for particular samples, indicating that the hydrolysis protocol, the further processing of hydrolysed samples and the performance of the ACE inhibition assay is standardised and accurate.

8.2 In Vivo SHR Tests and Results

In order to study the effect of hydrolysates on blood pressure, SHR studies were carried out. Primary effects on blood pressure and secondary effects on the development of organ damage were studied. SHR have a mean arterial blood pressure (MAPB) of about 190 mmHg, which is well above normal blood pressure.

The hydrolysates were fed to SHR rats by daily oral treatment via the drinking water. 52 rats were treated with 1000 mg/kg body weight per day of hydrolysate. Four hydrolysates were tested:
Hydrolysate A: lysozyme—alcalase
Hydrolysate B: ovotransferrin—newlase F
Hydrolysate C: ovomucin—alcalase
Hydrolysate D: egg white protein—alcalase Two methods were used to determine blood pressure, the tail-cuff method (measuring systolic blood pressure of rats under anesthesia or not under anaesthesia, SBP) and the telemetric method, whereby blood pressure measurements were taken every 5 minutes by an implanted telemetric device. Reference rats received placebos. The radio-telemetric technology makes it possible to continuously monitor arterial pressure, heart rate and physical activity as well as their circadian rhythms and their response to therapeutics in unrestrained animals for a longer period of time.

8.2.1 Tail-Cuff Results

The SBP of anaesthetized rats fed on hydrolysate A was lowered at day 65 from 201.7 to 183.8 mmHg, a blood pressure reduction of about 10%. It thus appears that at least Hydrolysate A is effective in vivo. For the other three hydrolysates the experiments are ongoing.

Also, ACE activity in the tissue (not in blood plasma) will be tested for ACE inhibition.

8.2.2 Telemetric Method

Lysozyme—alcalase and ovomucin—alcalase hydrolysates showed a significant blood pressure lowering effect in vivo.

Telemetry in Conscious Unrestrained Animals:

Initially, daily SBP increased over time in all TM-rats—hence, as would be expected in untreated SHR rats. However, at 5 weeks after onset of treatment individual patterns of daily SBP started to show a consistent decline in TM-rats receiving Hydrolysate A. The decline in SBP in TM-rats receiving Hydrolysate A lasted up to 7 weeks after onset of treatment, after which it stabilized. After 8 weeks of treatment, SBP had consistently decreased by approximately 10% in telemetric rats treated with Hydrolysate A.

8.2.3 Acute Treatment Effects of Lysozym/Alcalase in Anaesthetized SHR

This study was performed to establish the effects of acute oral treatment of anaesthetized SHR with lysozym/alcalase on blood pressure and plasma ACE activity.

Methods

Rats: SHR rats (382-440 g) were purchased via Harlan, Horst, The Netherlands from Harlan, Oxon, United Kingdom.

Housing: Rats were housed group-wise at the Central Animal Laboratory (UMCG, Groningen) and allowed to acclimatise for 1 week.

Surgery: At the day of the experiment, rats were anaesthetized and the carotid artery was cannulated for measurement of blood pressure. In addition to that, the jugular vein was cannulated to allow blood sampling for measurement of plasma ACE activity.

Protocol: At timepoint t=0, rats were administered the study drugs by means of oral gavage using a gastric tube. Blood samples were drawn immediately prior to gavage at t=0, as well as at t=0.5, t=1, t=2, t=3, t=4, t=5 and t=6 hr thereafter. Blood pressure was recorded (mean value every 10 min) throughout the 6 hr study period;

Study drugs: Rats were randomly administered either lysozym/alcalase or lysozym (both 1000 mg/kg; dissolved in 1 ml drinking water), or water only.

Results

Blood pressure: The effect of the study drugs on blood pressure was calculated as the percentage change from baseline in individual rats. Oral administration of a single dose of lysozym/alcalase (Hydro.A) caused a profound and transient reduction in systolic blood pressure (SBP). The maximal reduction in SBP was approx. 35% and was reached 1.5-2 hr after administration of lysozym/alcalase and maintained low for approx. another 2 hr. Thereafter—starting approx. at t=4 hr—SBP started to increase again, reaching 20% reduction at the end of the study period at t=6 hr. A very comparable pattern was seen after administration of lysozym (control), albeit that the maximal decrease in SBP was much smaller (approx. 15%). We also studied the effects of administration of water in these experiments; SBP also decreased after administration of water with a maximal decrease smaller than lysozym/alcalase and slightly bigger than lysozym only (i.e. response lying in between). However, the pattern in SBP changes obtained after water was clearly different from that of the former two, in particular more transient; at 2-3 hr after administration of water SBP had fully returned to baseline (i.e. 100%). Lysozym only is probably a better control for lysozym/alcalase than is water.

Plasma ACE-activity: The pattern of plasma ACE activity after lysozym/alcalase (Hydro.A) and lysozym (Control) very much followed the pattern of that seen for SBP. I.e. plasma ACE activity was maximally decreased by approx. 30% from baseline at t=2-t=3 hr after administration of lysozym/alcalase, before it started to raise again reaching approx. 95% of baseline values at t=6 hr. In contrast, maximal inhibition of plasma ACE-activity after lysozym only was approx. 10%.

The above findings clearly demonstrate the acute blood pressure lowering potential of lysozym/alcalase in anaesthetized SHR-rats; concomittant reduction in plasma ACE-activity suggests that this blood pressure lowering effect is due to inhibition of the renin-angiotensin system. Because the number of rats involved in this study was rather small, and because we wished confirm this effect preferably in conscious animals, we designed a third experimental study using TM measurements (hence, the TM method is not as stressful as the TC in conscious animals).

8.2.4 Acute Treatment Effects of Lysozym/Alcalase in Conscious SHR

This study was performed to establish the effects of acute oral treatment of conscious SHR with lysozym/alcalase on blood pressure and plasma ACE activity.

Methods

Rats: SHR rats (388-515 g) were purchased via Harlan, Horst, The Netherlands from Harlan, Oxon, United Kingdom, and housed group-wise at the Central Animal Laboratory (UMCG, Groningen).

Radiotelemetry: SHR rats (n=8) underwent surgery for placement of telemetric blood pressure transmitter device (TM) and a permanent catheter for blood sampling. The TM was implanted into the abdominal aorta distal to the left renal artery. The permanent catheter was implanted into the jugular vein and the other end tunneled subcutaneously to the head of the rat where it was fixated. Rats were then housed individually and allowed to recover for two weeks, after which collection of radiotelemetry data was started and continued for the entire study period.

Protocol: Rats were then allocated to a randomized treatment schedule with a single dose of lysozym/alcalase (LHA), lysozym (L), or water (H2O) at three different occasions on 3 different experimental days, with 2-3 (washout/control) days in between. Lysozym/alcalase and lysozym (both 1000 mg/kg) was dissolved in water and orally administered (total volume of approx. 1 ml solution) via a gastic tube; control rats were administered 1 ml of water only. Oral gavage on experimental days was always performed in the morning between 9:00-10:00 hr.

| | Rat 1 | Rat 2 | Rat 3 | Rat 4 | Rat 5 | Rat 6 | Rat 7 | Rat 8 |
|---|---|---|---|---|---|---|---|---|
| Day 1 (22-11-2004): | LHA | L | H2O | LHA | L | H2O | LHA | L |
| Day 2 (25-11-2004): | H2O | LHA | L | L | H2O | LHA | H2O | LHA |
| Day 3 (29-11-2004): | L | H2O | LHA | H2O | LHA | L | L | H2O |

Blood sampling: At the day of oral treatment approx. 0.5-1.0 hr before oral gavage, the permanent catheter was connected to an extended cannula that allows for blood sampling without further handling of the rats. A blood sample was drawn immediately before (t=0), and at t=0.5, 1, 2, 3, 4, 5, and 6 hr after oral gavage. Subsequently, blood samples were centrifuged at 1600G for 10 minutes at 4° C., plasma was snap-frozen, and stored at −80° C. until assay.

Plasma ACE-activity: ACE activity in the plasma tissue was determined according to the Hip-His-Leu method, as has been described before. In short, plasma samples are incubated with the ACE substrate Hippury-His-Leu 12.5 nM at 37° C. for exactly 10 minutes. The conversion of the substrate was stopped by adding 280 mM NaOH. Thereafter, 100 µl phtaldialdehyde was added for the labeling of free His-Leu. The amount of labeled Hid-Leu was fluorimetrically determined at excitation and emission wavelengths of 364 and 486 nm, respectively. Control samples were included in which the conversion of substrate was prevented by adding NaOH before the substrate Hippuryl-His-Leu.

Analysis of blood pressure data: The period of interest was considered the time roughly 1 hr before oral gavage on experimental days until 10 hr thereafter; i.e. from 8:00 until 19:00 hr. These time periods were obtained from the 3 experimental days for each rat, and then averaged for one specific treatment using data from all rats. The same time periods were also obtained from 6 non-experimental (control) days before and inbetween the experimental days for each rat, and then averaged for all rats.

Results

Lowering of SBP with LHA was observed within one hour and remained lower for at least 4 h compared to H2O. Also with L a lowering of SBP was observed, although with a delay of 1 h compared to LHA. This may be the result of the natural digestive process on L and, based on the relatively high dose, may be an indication that much smaller LHA does will be effective as well.

8.2.4.1 Acute Treatment Effects of Ovomucin/Alcalase in Conscious SHR

Methods

Rats: The above telemetric rats from 8.2.4 were used, except for one rat that had died spontaneously in the mean time. On experimental days, rats (n=7) were treated either with or without ovomucin/alcalase hydrolysate (1000 mg/kg), mixed with 3 ml of glucose water (10%) and presented to the rats in the morning (at approx. 10:00) on a flattened dish (for 30 min); on control days treatment consisted of glucose water only, and there where two days between control treatment and active treatment.

Analysis of blood pressure data: The period of interest was considered the time roughly 1 hr before oral treatment on experimental days until 8 hr thereafter; i.e. from 9:00 until 17:00 hr. These time periods were obtained from the 2 experimental days for each rat, and then averaged for ovomucin treatment or control treatment using data from all rats. The same time periods were also obtained from 4 non-experimental (control) days before and inbetween the experimental days for each rat, and then averaged for all rats.

Results

From one SHR-rat, systolic blood pressure data were extremely low and these were excluded from further analysis. On experimental days, most rats finished the 3 ml glucose-water within 10 min. Drinking of glucose water went along with an increase in systolic blood pressure; i.e. this is similar to that observed after intake by gastric tube in the above study although the degree to which SBP increases was considerably smaller after intake by glucose-water (approx. 10 mmhg) as compared to oral intake by gastric tube (approx. 25 mmHg). For that matter, this effect was not observed on control days when no treatment was given. Compared to control treatment with glucose-water only, active treatment with glucose-water containing the ovomucin/alcalase hydrolysate resulted in a faster and more pronounced reduction in SBP. Maximal reduction after ovomucin/alcalase hydrolysate was reached within one hour after intake (approximately 15 mmHg), hence, which is very similar to the time-frame observed in awake rats in the above study.

Example 9

Enrichment of Hydrolysates by Membrane Filtration

To study whether an enrichment of small peptides and a resulting increased in ACE inhibitory activity could be achieved, two hydrolysed egg white proteins, ovotransferrin and lysozyme, were fractionated by membrane filtration (using Polyethersulfon ultrafiltration membranes with a cut-off of 2 kD and 10 kD).

The polyethersulfon ultrafiltration membrane was used in an Amicon test cell for flat membranes. A volume of 15 ml of a 5% solution of the protein hydrolysate was concentrated to 5 ml (15%) and 5 ml of water was added. This solution was again concentrated to 5 ml (washing step). The washing step was repeated two times more. The permeates of the initial filtration and of the wash steps were combined and freeze dried. The freeze dried permeates were stored at 4° C. and tested for ACE inhibiting activity.

The set up of this experiment was as follows:
Two hydrolysates: ovotransferrin/promod258 and lysozyme/alcalase
Two membranes, one with a cut-off of 2 kD and the other with a cut-off of 10 kD
Following fractionation the various samples (feed, permeate and retentate) were treated without and with in vitro digestion simulation, in which the time of pepsin incubation (simulating the hydrolysis in the stomach) was varied between 0 and 120 minutes
Pepsin incubation was at pH2, 37° C.
Trypsin/α-chymotrypsin incubation was at pH6.5, 37° C., for 2.5 h
After freeze-drying of the samples the IC50 (mg/ml) values of the fractions were determined:

| Hydrolysate sample | Sub-sample | No digestion simulation | Trypsin/α-chymotrypsin incubation preceded by: | | | | Weight (%) |
| --- | --- | --- | --- | --- | --- | --- | --- |
| | | | 0' pepsin | 10' pepsin | 30' pepsin | 120' pepsin | |
| Ovotransferrin/ Promod | September 2003 | 0.16 | — | — | 0.16 | 0.15 | |
| | feed | 0.16 | 0.18 | — | — | — | |
| | 2 kD ret. | 0.63 | 0.65 | 0.38 | 0.32 | 0.33 | 64.8 |
| | 2 kD perm | 0.09 | 0.12 | — | 0.19 | 0.17 | 35.2 |

-continued

| | | IC50 (mg/ml) | | | | | |
|---|---|---|---|---|---|---|---|
| | | No | Trypsin/α-chymotrypsin incubation preceded by: | | | | |
| Hydrolysate sample | Sub-sample | digestion simulation | 0' pepsin | 10' pepsin | 30' pepsin | 120' pepsin | Weight (%) |
| | 10 kD ret. | 1.14 | 0.56 | 0.82 | 0.35 | 0.30 | 52.9 |
| | 10 kD perm | 0.11 | 0.11 | 0.12 | 0.11 | 0.13 | 47.1 |
| Lysozyme/ Alcalase | September 2003 feed | 0.14 0.10 | — 0.12 | — — | 0.12 — | 0.12 — | |
| | 2 kD ret. | 0.30 | 0.17 | 0.17 | 0.19 | 0.17 | 66.6 |
| | 2 kD perm | 0.07 | 0.05 | — | 0.07 | 0.06 | 33.4 |
| | 10 kD ret. | 0.53 | 0.26 | 0.18 | 0.21 | 0.23 | 48.9 |
| | 10 kD perm | 0.06 | 0.13 | 0.12 | 0.06 | 0.08 | 51.1 |

As compared to the feed fractions the ACE inhibitory activity of the permeate fractions increased by up to a factor two. This increase was observed with the 10 kD membrane in the case of ovotransferrin and with the 2 kD membrane for lysozyme.

This example shows that membrane filtration can be used to enrich hydrolysates for bioactive peptides, thereby enriching the ACE inhibitory activity of the hydrolysate. Enrichment can be used to reduce the amount of material that must be consumed on a regular (e.g. daily) basis to achieve an effect and eases the incorporation into food supplements and functional food products due to a volume reduction.

Example 10

Effect of Storage Time and Temperature of Eggs on Ace Inhibitory Activity

The influence of storage time and temperature was investigated with eggs that were processed directly (separation of egg white from egg yolk, followed by hydrolysis of the egg white fraction with alcalase), or after storage for 6 weeks at 4° C. or at room temperature.

Hydrolysis with Alcalase: a) for 3 h or b) for 5 h (addition of extra enzyme after 3 h)

Following hydrolysis the fractions were freeze-dried and the powder fractions were stored at room temperature. The ACE inhibitory activity of all the fractions was determined in the same assay. The experiment was carried out twice.
Effect of Storage Time and Temperature of Eggs on Egg White Protein Ace Inhibitory Activity:

| Hydrolysis | | IC50 value (mg/ml) after indicated treatment | | |
|---|---|---|---|---|
| | | direct (fresh) | 6 weeks at 4° C. | 6 weeks at RT[1] |
| 3 hour | repeats | 0.25 | 0.35 | 0.53 |
| | | 0.47 | 0.45 | 0.61 |
| | mean | 0.36 | 0.40 | 0.57 |
| 5 hour | repeats | 0.26 | 0.34 | 0.32 |
| | | 0.39 | 0.34 | 0.34 |
| | mean | 0.33 | 0.34 | 0.33 |

[1]Room Temperature

Hydrolysis for 5 hours yields hydrolysates with better and more reproducible activity than hydrolysis for 3 hours.

The experiment showed that for optimal activity of egg white protein hydrolysates with respect to ACE inhibiting activity the eggs may be used directly, or can be stored for at least 6 weeks at 4° C. or at room temperature.

Example 11

Bitterness of Hydrolysates

Hydrolysates were sensorically analysed by three volunteers in order to assess bitter taste. Hydrolysate powders were dissolved in water (15-20 mg/ml), or water and glucose.

| Hydrolysate | Water | Water + 0.44% glucose | Water + 0.88% glucose |
|---|---|---|---|
| Ovotransferrin-newlaseF | bitter | bitter | bitter |
| Ovomucin - alcalase | neutral | | |
| Egg-white-alcalase | Bitter/sour | Less bitter | Less bitter (same as for 0.44% glucose) |
| Lysozyme - alcalase | neutral | | |

Two hydrolysates tasted bitter, while two did not have a bitter taste. The bitterness of egg white-alcalase could slightly be masked by addition of glucose. For a number of hydrolysates the addition of flavourings or other taste masking compounds will be required in the food products, such as maltodextrin, aspartame, inulin, etc.

The taste had no effect on the willingness of rats to consume the hydrolysates.

Example 12

Food Supplements and Food Products

Tablet or Sachet
A tablet (or sachet) with the following composition is made:
  250 mg target protein hydrolysate per tablet (about 60% volume of tablet)
    40% volume comprising cornstarch (20%), cellulose (15%), polysaccharide (0.5%), lubricating and glossing agents (3%), others (1.5%).

Example 13

Molecular Weight Distribution of Protein Hydrolysates

Molecular weight distribution (MWD) of the protein hydrolysates was performed by gel permeation chromatography (GPC), using a Superdex Peptide PE 7.5/300 column (Amersham Biosciences, Uppsala, Sweden). This column has a MW separation range of 100 to 7000. The column was run in 30% acetonitrile containing 0.1% TFA, conditions shown to be ideal for analysis of protein hydrolysates by A&F. The column was calibrated using standard peptides with known molecular weight (see Table below). Standards and hydrolysate samples were dissolved in the standard eluent at a peptide concentration of 5 mg/ml. Before injection (200 µl) the samples were centrifuged in order to remove insoluble particles. The elution pattern was monitored at 214 nm.

| Standard | Mw |
|---|---|
| L-Leucine | 131.2 |
| L-Arginine | 174.2 |
| VVYV | 478.5 |
| VVYK | 507.6 |
| VVYR | 535.6 |
| Insulin Chain B-oxidase | 3,496 |
| Aprotinin from Bovine Lung | 6,500 |
| Cytochrome C from Bovine Heart type V-A | 12,327 |
| Lysozyme.HCl | 14,300 |

The calibration curve is not shown.

MWDs of protein hydrolysates are expressed in terms of the fraction (%) of peptides that have a predefined molecular weight range: smaller than 500 Da, between 500-1000 Da and larger than 1000 Da. This corresponds with peptides of the following lengths: less than 4-5 amino acids, 4-9 amino acids or larger than 9 amino acids.

Results:

| Hydrolysate | DH (%) | IC50 (mg/mL) | % < 500 Da | % 500-1000 Da | % > 1000 Da |
|---|---|---|---|---|---|
| Egg White/Alcalase (LS 250903) | 31.9 | 0.46 | 91.7 | 4.6 | 3.7 |
| Lysozyme/Alcalase (LS 250903) | 34.5 | 0.11 | 53.4 | 16.7 | 29.9 |
| Lysozyme/Alcalase (Sup 101104) | 34 | 0.15 | 89.4 | 0.9 | 9.7 |
| Lysozyme/PEM (LS 250903) | 34 | 0.12 | 99.1 | 0.8 | 0.1 |
| Lysozyme/PEM (LS 250903) | 34 | 0.12 | 99.2 | 0.7 | 0.0 |
| Ovomucin/Alcalase (170604) | 12 | 0.54 | 85.1 | 10.0 | 4.9 |
| Ovomucin/Alcalase (281004_1) | 21.7 | 0.39 | 99.1 | 0.9 | 0.0 |
| Ovomucin/Alcalase (281004_2) | 23.9 | 0.21 | 97.7 | 0.8 | 1.6 |
| Ovomucin/Alcalase (5ml5h 2 BB 211004) | 5 | 0.76 | 69.7 | 16.4 | 13.9 |
| Ovomucin/Alcalase (LS 250903) | 14.9 | 0.73 | 44.9 | 21.7 | 33.4 |
| Ovotransferrin/Promod258P (LS 250903) | 27.3 | 0.15 | 70.2 | 10.7 | 19.1 |

The results show that there is a correlation between the degree of hydrolysis of the target protein and the IC50 activity. Especially, a degree of hydrolysis of at least about 20%, more preferably at least about 30% results in hydrolysates with high ACE inhibitory activity.

Example 14

In Vivo Studies in Human with Egg Peptides that Significantly Reduced Blood Pressure in Spontaneously Hypertensive Rats Composition of Lysozyme Hydrolysate for In Vivo Human Study:

The composition of the ACE inhibiting lysozym/alcalase hydrolysate was determined:
90% lysozyme
1.8% alcalase
5% NaOH
3.2% water Lysozyme Hydrochloride was from Belovo (Schoterweg 14, 8462 TD Rotstergaast)
  is a minor protein from egg white purified by ion-exchange chromatography
  99% purity by SDS-PAGE en HPLC chromatography
Alcalase Food Grade van Novozymes, Alcalase 2.4 L
  clear, red-brown liquid
  enzyme concentration 2.3 AU/liter
  density approx. 1.18 g/ml
  Alcalase is produced from a selected strain of Bacillus licheniformis
  bacterial protease, endopeptidase
NaOH pellets van Merck
  33% solution used to adjust oh during hydrolysis to 8
  For a 3% lysozyme (100 ml) solution approximately 500 µl of a 1 M NaOH solution was needed to set the pH to 8 (500 µl of 1 M NaOH=0.02 g NaOH for 3 g lysozyme) After addition of the enzyme addition of NaOH is still required to keep the pH at 8; hence, a few percent of NaOH is present in the end-product.

Human Study:

Final permission of the METc (Medical Ethical Trial committee) of the University Medical Center Groningen (UMCG) for studies with functional food products in humans has been obtained Human volunteers (n=5) received in the drink below a single dose of either lysozym/alcalase or an appropriate placebo on two different experimental days. Blood pressure was measured immediately before intake and up to 6 h thereafter. In addition to that, blood samples were obtained immediately before and at specific time points after intake, and analyzed for ACE-activity.

Recipe Drink:
  20 g hydrolysate
  40 g Karvan Cévitan "Red Grapefruit"
  60 g water
Pasteurized for 20 minutes at 90° C.
Microbiologically analysed by Siliker (Ede): OK.
  Composition Karvan Cévitan Red Grapefruit: 60% fruit without colourings; 4 vitamines added; Fruit juice concentrate 60% (red grapefruit, elderberry, rose hip) of which 54% red grapefruit; other constituents: sugar, glucose-fructose juice, food acid: citric acid, flavour, vitamines, preservative: potassium sorbate.
  Controle drink: idem, but without hydrolysate.
Results The trial involved 5 persons that received the hydrolysate. Two weeks later 3 of these 5 persons were available for the control. The mean blood pressure was followed over a time period of 6 hours. Compared to the control an average lowering of the blood pressure of about 5 to 6% was measured showing a clear effect of the hydrolysate. The effect was observed within 1 hour after consumption of the hydrolysate and was maximal after 1.5. At 3 h and 6 h (last time point measured) the decrease in mean arterial pressure was comparable to that at 1.5 h. The average plasma ACE activity in the hydrolysate study showed a peak decrease within 1 h after consumption of the hydrolysate and after 3 h returned to the level at the start.

The human study is still ongoing.

The invention claimed is:

1. A food product or food supplement, comprising a *Bacillius licheniformi* endoproteinase hydrolysate of a lysozyme, wherein at least 30% of the hydrolysate are peptides of the lysozyme that have a molecular weight of less than 0.5 kD.

2. An enzymatic protein hydrolysate, wherein said hydrolysate is obtained by *Bacillius licheniformi* endoproteinase hydrolysis of a lysozyme and wherein at least 30% of the hydrolysate are peptides of the lysozyme that have a molecular weight of less than 0.5 kD.

3. A method for making a protein hydrolysate with anti-hypertensive activity, comprising the steps of:
    (a) providing a liquid solution comprising a lysozyme;
    (b) adjusting the pH of said solution to a pH suitable for *Bacillius licheniformi* endoproteinase; and
    (c) adding *Bacillius licheniformi* endoproteinase to said solution and incubating the solution for a suitable period at a suitable temperature to obtain a hydrolysate of the lysozyme wherein at least 30% of the hydrolysate are peptides of the lysozyme that have a molecular weight of less than 0.5 kD.

4. The method according to claim 3, further comprising a step (e) of filtering said solution through a membrane filter and obtaining a permeate which is enriched for active target peptides.

5. An anti-hypertensive protein hydrolysate, said hydrolysate obtained by the method according to claim 3.

6. The food product or food supplement according to claim 1, wherein said product or supplement is in the form of a liquid, solid or semi-solid.

7. A food product or food supplement, said food product or food supplement comprising the hydrolysate according to claim 5.

8. The enzymatic protein hydrolysate according to claim 2, wherein the proportion of di- and/or tri peptides in the hydrolysate is at least 50%.

9. The enzymatic protein hydrolysate according to claim 2, wherein at least 50% of the hydrolysate are peptides that have a molecular weight of less than 0.5 kD.

10. The food product or food supplement according to claim 1, wherein the proportion of di- and/or tri peptides of lysozyme in the hydrolysate is at least 50%.

11. The food product or food supplement according to claim 1, wherein at least 50% of the hydrolysate are peptides that have a molecular weight of less than 0.5 kD.

12. A method of reducing blood pressure or reducing the risk of developing high blood pressure comprising administering a food product or food supplement comprising a *Bacillius licheniformi* endoproteinase hydrolysate of a lysozyme, wherein at least 30% of the hydrolysate are peptides of the lysozyme that have a molecular weight of less than 0.5 kD.

13. A food product or food supplement comprising the enzymatic protein hydrolysate according to claim 2.

* * * * *